United States Patent

Mann et al.

[11] Patent Number: 5,856,114
[45] Date of Patent: Jan. 5, 1999

[54] IMMUNOLOGIC DETECTION OF FACTOR VA FRAGMENTS IN HEMORRHAGIC AND THROMBOTIC CLINICAL SETTINGS

[75] Inventors: Kenneth G. Mann, Shelburne; Michael Kalafatis, Burlington, both of Vt.

[73] Assignee: The University of Vermont, Burlington, Vt.

[21] Appl. No.: 606,549

[22] Filed: Feb. 26, 1996

Related U.S. Application Data

[63] Continuation of Ser. No. 210,936, Mar. 21, 1994, abandoned.

[51] Int. Cl.$^6$ ..................................................... C12Q 1/56
[52] U.S. Cl. ............................... 435/13; 436/69; 530/381
[58] Field of Search ............................ 435/7.4, 7.9, 9.92, 435/12, 7.1; 436/811, 69; 530/381, 384

[56] References Cited

U.S. PATENT DOCUMENTS 5,049,491   9/1991   Mann et al. ............................ 435/7.92

OTHER PUBLICATIONS

Odegaard et al. "Proteolysis of Factor Va by Factor Xa and Activated Protein C", *The Journal of Biological Chemistry*, vol. 262, No. 23 (Aug. 15, 1987), pp. 11233–11238.

Guinto et al. "The Complete cDNA Sequence of Bovine Coagulation Factor V", *The Journal of Biological Chemistry*, vol. 267, No. 5 (Feb. 15, 1992), pp. 2971–2978.

R.J. Jenny et al. "Complete cDNA and derived amino sequence of human factor V", *Proc. Natl. Acad. Sci. USA*, Biochemistry, vol. 84, pp. 4846–4850, 1987 (Jul).

M. Kalafatis et al. "The Mechanism of Inactivation of human Factor V and Human Factor Va by Activated Protein C", *The Journal of Biological Chemistry*, vol. 269, No. 50, pp. 31869–31880, 1994 (Dec).

M. Kalafatis et al. "Characterization of the Molecular Defect in Factor $V^{R506Q}$", *The Journal of Biological Chemistry*, vol. No. 8, pp. 4053–4057, 1995 (Feb.).

M. Kalafatis et al. "Biochemical Prototype for Familial Thrombosis", *Arteriosclerosis, Thrombosis, and Vascular Biology*, vol. 15, No. 12, 1995 (Dec).

Omar M.N. et al., "Inactivation of Factor Va by Plasmin." Journal of Biological Chemistry 262 (20): 9750–55, 1987.

Odegaard B. et al., "Proteolysis of Factor Va by Factor Xa and Activated Protein C." Journal of Biological Chemistry 262 (23): 11233–11236.

Guinto E. R. et al. , "The Complete DNA Sequence of Bovine Coagulation Factor V." Journal of Biological Chemistry 267 (5): 2971–2978, 1992.

*Primary Examiner*—Jeffrey Stucker
*Attorney, Agent, or Firm*—David G. Conlin; Ernest V. Linek; Robert L. Buchanan

[57] ABSTRACT

The present invention is directed to immunochemical detection procedures, e.g., using both Western blotting and direct immunoassays, for fragments of Factor Va, which can thus be used; (a) in a predictive manner to evaluate the existence and/or extent of a thrombotic complication; (b) to monitor the efficacy of prophylaxis for a thrombotic condition; and (c) as a means to evaluate potential risk of hemorrhage during thrombolytic therapy.

3 Claims, 13 Drawing Sheets

| CYCLE NO. | a | b | c | d | e | f | g |
|---|---|---|---|---|---|---|---|
| 1 | R (0.71) / A (0.52) | R (3.4) / A (4.43) | A (51.35) | S (37.61) | N (49.69) | G (26.18) | G (5.20) |
| 2 | A (0.76) / - - | A (6.61) / S (0.80) | K (36.64) | N (59.88) | P (46.09) | I (21.06) | I (9.70) |
| 3 | S (0.13) / - - | S (1.10) / S (1.00) | L (55.82) | T (45.09) | K (24.24) | Q (17.75) | Q (7.75) |
| 4 | S (0.10) / E (0.21) | S (1.20) / E (1.33) | R (26.60) | G (47.62) | K (30.63) | R (11.62) | R (6.15) |
| 5 | E (0.32) / V (0.20) | E (2.66) / V (1.20) | Q (34.68) | N (44.77) | L (32.59) | A (17.32) | A (6.70) |
| 6 | V (0.30) / K (0.11) | V (2.29) / K (0.3) | F (30.00) | R (29.84) | T (17.23) | A (20.18) | A (9.24) |
| 7 | K (0.13) / N (0.20) | K (0.70) / N (1.46) | Y (26.70) | K (30.46) | R (23.00) | D (14.49) | D (6.13) |
| 8 | N (0.3) / - - | N (2.23) / S (0.20) | V (30.37) | Y (36.18) | D (23.84) | I (14.07) | I (6.09) |
| 9 | - -  H (0.15) | S (0.48) / H (0.60) | A (30.39) | Y (45.81) | Q (19.48) | E (9.39) | E (4.44) |
| 10 | H (0.20) / E (0.20) | H (0.60) / E (0.60) | A (37.72) | Y (47.32) | R (13.24) | Q (9.37) | Q (4.30) |
| 11 | - -  F (0.61) | E (1.44) / F (0.20) | Q (19.48) | | R (22.08) | | |
| 12 | - - | F (0.83) / - - | S (3.03) | | H (14,55) | | |
| 13 | A(0.10) | H (0.60) / A (0.61) | I (12.87) | | I (15.73) | | |
| 14 | | A (1.21) / - - | R (11.79) | | K (9.19) | | |
| 15 | | I (0.65) / N (0.40) | W (4.30) | | R(10.11)/F(11.5) | | |
| 16 | | N (0.62) / G (0.20) | N (9.24) | | W (6.70) | | |
| 17 | | G (0.70) / M (0.22) | Y (5.06) | | E (9.04) | | |
| 18 | | M (0.25) / - - | R (4.96) | | Y (9.96) | | |
| 19 | | I (0.70) / - - | P (5.85) | | F (15.69) | | |
| 20 | | Y (0.36) / - - | E (4.70) | | I NQ | | |

FIG. 6B

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 10 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:1:

```
Arg  Ala  Ser  Ser  Glu  Val  Lys  Asn  Ser  His
 1                  5                        1 0
```

( 2 ) INFORMATION FOR SEQ ID NO:2:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:2:

```
Ala  Ser  Ser  Glu  Val  Lys  Asn  Ser  His
 1                  5
```

IMMUNOLOGIC DETECTION OF FACTOR VA FRAGMENTS IN HEMORRHAGIC AND THROMBOTIC CLINICAL SETTINGS

This application is a continuation of U.S. Ser. No. 08/210,936, filed Mar. 21, 1994, now abandoned.

CROSS-REFERENCE TO RELATED APPLICATIONS AND STATEMENT OF GOVERNMENT SUPPORT

This application was funded in part by the following grants from the National Institutes of Health; Merit Award R37 HL34575, Training Grant T32 HL07594 and Grants P01 HL46703 and R01 HL46973. Thus, the government of the United States has certain rights in this invention.

This application is related to the invention described and claimed in Mann et al., U.S. Pat. No. 5,049,491, entitled "IMMUNOLOGIC DETECTION OF FACTOR V(Va) FRAGMENTS IN HEMORRHAGIC AND THROMBOTIC CLINICAL SETTINGS," the disclosure of which is hereby incorporated herein by reference.

BACKGROUND OF THE INVENTION

The formulation of α-thrombin is a central event during the blood coagulation cascade. Prothrombin is activated to α-thrombin by the prothrombinase complex which is composed of the serine protease factor Xa and the protein cofactor factor Va assembled on a membrane surface in the presence of $Ca^{2+}$ ions (1)[1]. In the absence of factor Va, factor Xa is capable of activating prothrombin to α-thrombin (2); however, the prothrombinase complex is 5 orders of magnitude more efficient in generating α-thrombin than factor Xa acting along (2). Once formed, α-thrombin acts as a procoagulant enzyme, catalyzing the formulation of the fibrin clot by converting soluble fibrinogen to insoluble fibrin polymers (3). α-Thrombin also binds to the endothelial cell receptor thrombomodulin, and the resulting α-thrombin-thrombomodulin complex exhibits altered proteolytic specificity (4,5). This complex catalyzes the activation of protein C to form the anticoagulant enzyme activated protein C (APC).[1]

[1] Reference articles are indicated herein by (number) and are identified before the claims under the heading CITED REFERENCES.

Activation of bovine protein C occurs by cleavage of a single peptide bond ($Arg^{171}$) located at $Arg^{14}$ of the heavy chain of protein C (5). Bovine protein C is also activated by the factor Xz-thrombomodulin complex which produces an APC molecule (6). The proteolytic APC antithrombotic function is expressed by inactivating factor Va and factor VIIIa, two important cofactors of the blood coagulation cascade (7, 8).

Factor V circulates s a single chain procofactor ($M_4$ 330,000). The CDNA sequence for bovine factor V and deduced amino acid sequence have been determined (9). The active form of the protein, factor Va (10-12), is composed of a heavy chain ($M_r$ 94,000) containing the NH2-terminal part of the procofactor (residues 1–713) and a light chain (Mr 74,000) containing the COOH-terminal part of the molecule (amino acids 1537–2183; Ref. 9). The two chains are noncovalently associated (13, 14).

The inactivation of factor Va by APC occurs in the presence as well as in the absence of a lipid bilayer or platelet surface (15-20). Previous studies have demonstrated that bovine factor Va in the absence of a lipid bilayer and in the presence of high concentrations of APC is slowly and partially inactivated (20). In contrast, earlier kinetic data showed that in the presence of an anionic phospholipid membrane surface factor Va is rapidly and completely inactivated by APC (15-17). Recent data also showed that bovine factor Va phosphorylation at the COOH-terminal end of the heavy chain on $Ser^{690}$ results in a molecule that is more sensitive to APC inactivation that its native counterpart (21). The identification of the APC proteolytic cleavage sites in the cofactor observed in the absence of phospholipid has been correlated with the partial inactivation of factor Va. Thus, although studies demonstrate that inactivation of the cofactor is a rapid phenomenon in the presence of a membrane surface (15-17), the chemical studies relating the APC effect on the factor Va molecule functions have been performed in the absence of lipids (18,22,23).

APC cleavage of the bovine factor Va heavy chain at $Arg^{505}$ and $Arg^{662}$ (and $Arg^{506}$ in the human sequence) is responsible for the partial inactivation of the cofactor (20). However, in these studies even after prolonged incubation of factor Va with high APC concentrations (i.e., 4 h, 1:1 molar ratio) in the absence of a membrane surface the cofactor still retained 30–35% of its initial cofactor activity (20). Thus, the contribution of the membrane to the mechanism by which APC inactivates factor Va has not been elucidated yet.

It has been shown that vitamin K-dependent protein S plays a role in the APC inactivation process only in the presence of a phospholipid membrane (24,25). Its functions have not been established clearly yet, but protein S must play an important role as an antithrombotic agent since studies demonstrated that familial heterozygous deficiency of protein S is associated with venous and arterial thrombosis (26,27).

SUMMARY OF THE INVENTION

As a consequence of the central position of Factor V in the blood clotting scheme, activation to Factor Va and the consequences of inactivation, Factor V provides the ideal marker to evaluate the existence of a thrombotic condition or the potential for hemorrhagic complication.

Thus, the present invention is directed to immunochemical detection procedures, e.g., using both Western blotting and direct immunoassays, for specific Factor Va fragments, which can thus be used; (a) in a predictive manner to evaluate the existence and/or extent of a thrombotic complication; (b) to monitor the efficacy of prophylaxis for a thrombotic condition; and (c) as a means to evaluate potential risk of hemorrhage during thrombolytic therapy.

In each of the above described conditions (i.e., thrombosis or hemorrhage) specific sets of Factor Va fragments are produced and analytical methodology currently exists for their quantitative evaluation in blood samples.

Hence, the present invention is particularly directed to quantitative and qualitative assay techniques useful for determining the amount and/or presence of Factor Va in mammalian blood and/or plasma samples, which can be used in the clinical diagnosis of thrombosis and hemorrhagic risk.

The present invention was based in part upon our previous studies which established the APC inactivating cleavage sites on the bovine cofactor and the relation between proteolysis and inactivation of the cofactor in the presence and absence of a phospholipid membrane. The role of protein S as a cofactor for APC specificity as well as the role of factor Xa in the prevention of the inactivation of factor Va by APC was also found to be similar in the human system as previously detected in the bovine system. The data described herein in detail are thus the bovine data, which it is believed correlates well with human data and is thus empirically transferrable thereto.

DETAILED DESCRIPTION OF THE PREFERRED EMBODIMENTS

Figure 1A:
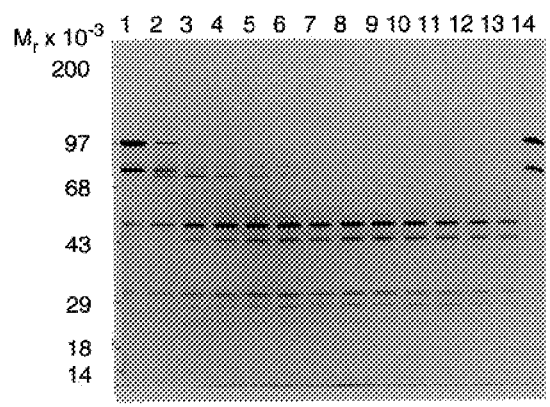
FIG. 1, in panels A, B, C, D, E and F, illustrates the proteolytic inactivation of factor Va by APC.
Figure 1B:
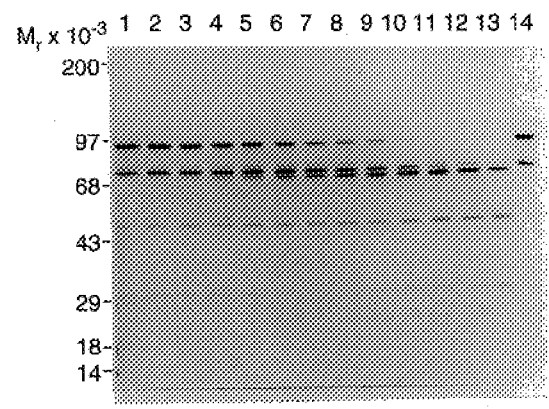
Figure 1D:
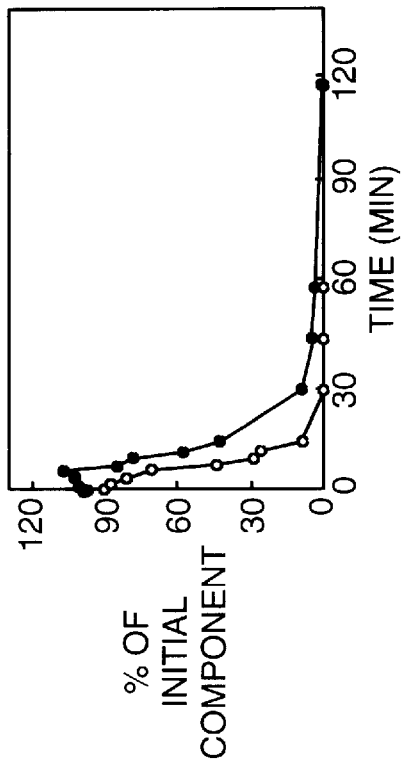
Figure 1F:
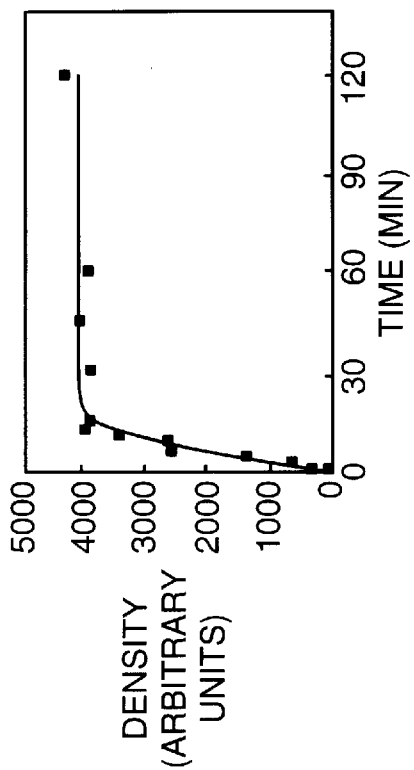
Figure 1C:
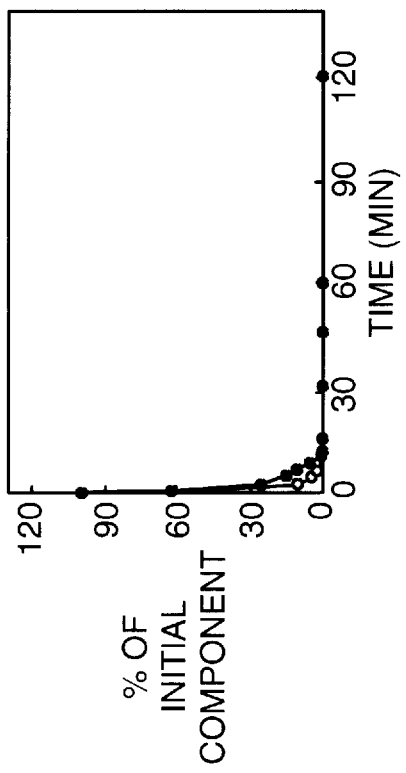
Figure 1E:
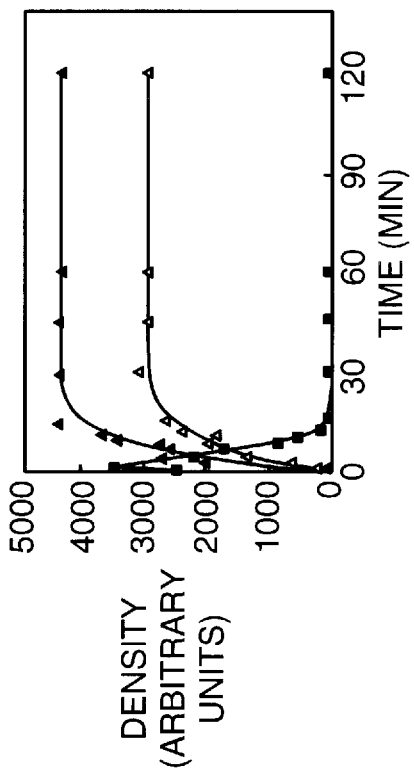

Human factor Va (HFVa) the cofactor for the prothrombinanse complex is inactivated by activated protein C (APC) after cleavage of the heavy chain ($HFVa_{HC}$). The mechanism of HFVA inactivation by APC was analyzed in the presence of APC with and without phospholipid vesicles (75% phosphatidylcholine (PC) and 25% phosphatidylserine (PS)). Membrane-bound HFVa losses 90% of its initial cofactor activity after 10 min incubation with APC in the presence of PCPS vesicles. No cofactor activity is observed after 2 h incubation of the membraane-bound cofactor with APC. In the absence of PCPS, the cofactor is cleaved but retains 70% of its initial cofactor activity after 2 h incubation with APC. The cleavage pattern of the $HFVa_{HC}$ in the absence of PCPS vesicles is different form the cleavage of the cofactor when incubated with APC in the presence of phospholipid membrane.

In the absence of a membrane surface or in the presence of phospholipd vesicles exclusively composed of PC cleavage of $HFVa_{HC}$ at $Arg^{506}$ results in a $M_r$=75,000 fragment which contains the $NH_2$-terminal portion of the $HFVa_{HC}$ (residues 1–506), and a carboxyl-terminal $M_r$=28,000 fragment (residues 507–709) which is further cleaved by APC at the COOH-terminus to generate a $M_r$=21,000 fragment.

In contrast, in the presence of PCPS vesicles the complete loss of activity is correlated with the cleavage of the $M_r$=75,000 fragment and the appearance of $M_r$=40,000 and $M_r$=30,000 fragments. A comparison of the $NH_2$-terminal sequence of the $M_r$=30,000 fragment with the sequence of human factor V indicated a match with residues 307–506 of $HFVa_{HC}$ demonstrating cleavage by APC at $Arg^{306}$. No cleavage of the light chain of the cofactor ($HFVa_{LC}$) is observed in the presence as well as in the absence of PCPS vesicles after two hours incubation with APC. Thus, a specific APC cleavage site is exposed when the cofactor is bound to PCPS. These data demonstrate that: 1) the presence of a membrane is essential for the complete inactivation of HFVa by APC; 2) cleavage at $Arg^{506}$ only partially inactivates the cofactor; and 3) cleavage at $Arg^{306}$ which is anionic lipid dependent is required for the complete inactivation of HFVa.

The present invention will now be described in detail by reference to the drawings accompanying this application.

FIG. 1 Proteolytic Inactivation of Factor Va by APC.

Factor Va (200 nM) was incubated with APC (10 nM) in the presence of PCPS vesicles (15 μM, panels A, C, and E) and in the absence of phospholipid (panels B, D an dF) at 37° C. At selected time intervals aliquots were withdrawn from the mixture and either assayed for factor Va cofactor activity (depicted on FIG. 2) or mixed immediately with 2% SDS, 2% β-mercaptoethanol, heated at 90° C., and analyzed as illustrated by 5–15% linear gradient SDS-PAGE. Panel A, SDS-PAGE representing proteolysis of membrane-bound factor Va by APC. Lane 1, factor Va control, no APC; lanes 2–13, factor Va and APC at 30 s and at 2, 4, 6, 8, 10, 12, 15, 30, 45, 60, and 120 min; lane 14, membrane-bound factor Va, no APC after incubation at 37° C. for 120 min. The positions of the molecular weight markers are indicated on the left. Panel B, SDS-PAGE representing proteolysis of factor Va by APC in the absence of PCPS (same time points as panel A). Panels C and D depict the disappearance of the heavy chain (open circles) of the cofactor as a function of time as assessed by scanning densitometry of the gels shown in panels A and B. The values obtained in panels A and B, lane 1, for the heavy and light chains were arbitrarily determined as 100% in panels C and D, respectively. Panel E represents the disappearance of the $M_r$70,000 fragment of the heavy chain (filled squares) and the appearance of the $M_r$40,000 (filled triangles) and the $M_r$ 28,000 (open triangles) as a function of time as assessed by scanning densitometry of the gel shown in panel A. Panel F represents the appearance of the $M_r$70,000 fragment after scanning the gel depicted in panel B.

Figure 2:
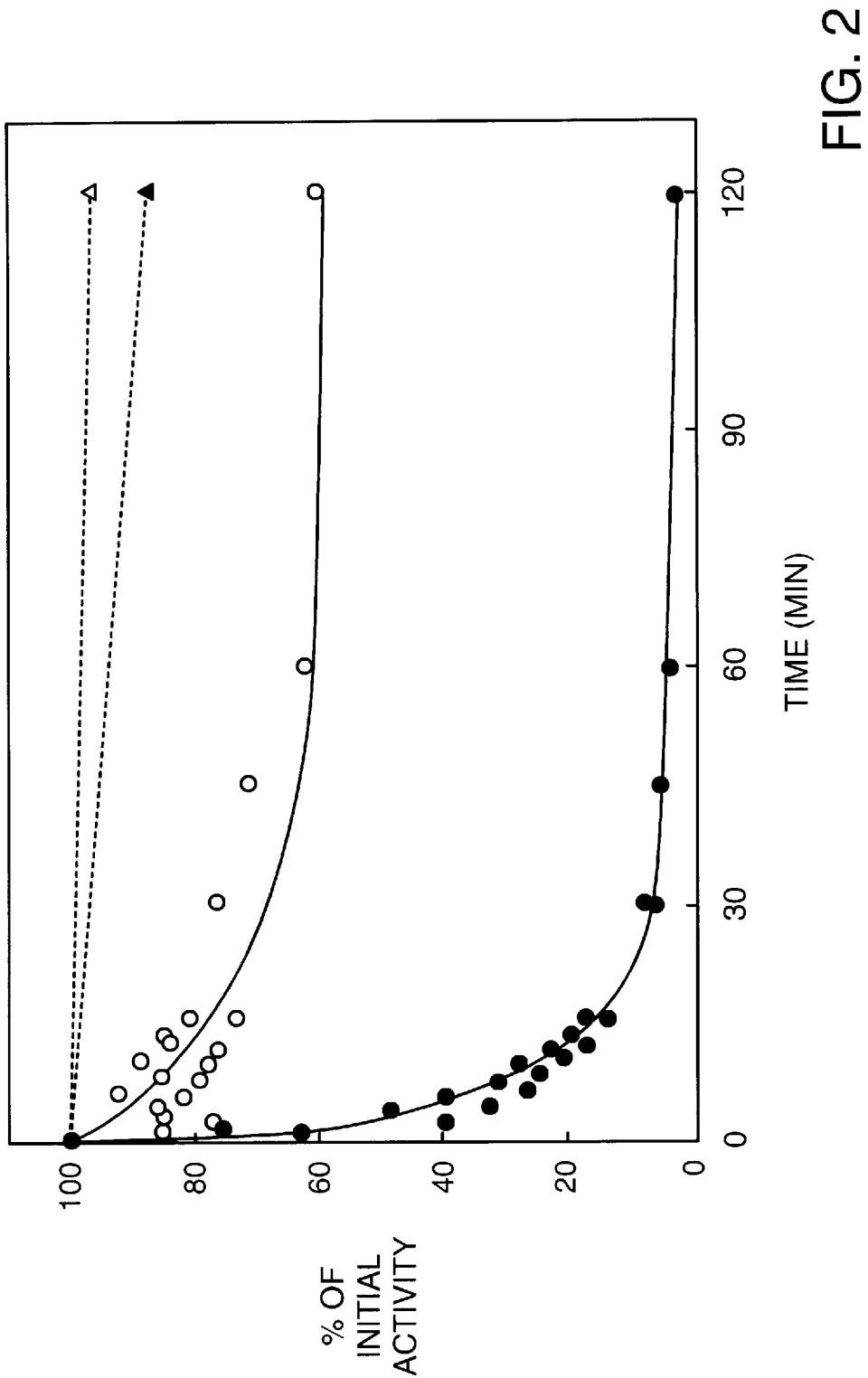
FIG. 2 illustrates the inactivation of factor Va by APC.

FIG. 2. Inactivation of Factor Va by APC.

Factor Va was incubated with APC as described below in the Examples, and as described above with reference to FIG. 1, i.e., in the absence or presence of PCPS. FIG. 1 illustrates the results obtained from two different experiments. During one of the experiments the time points were assessed for cofactor activity and analyzed by SDS-PAGE (illustrated in FIG. 1, panels A and B).

In FIG. 2, the initial rates of thrombin formation were calculated and plotted as percent of initial cofactor activity as a function of time after adding APC. Open circles represent factor Va treated with APC in the absence of PCPS; the filled circles depict membrane-bound factor Va treated with APC. The open triangle represents a control experiment, showing factor Va incubated in the absence of APC and PCPS for 2 h at 37° C.; the filled triangle shows factor Va incubated with PCPS in the absence of APC after a 2-h incubation at 37° C.

Figure 3:
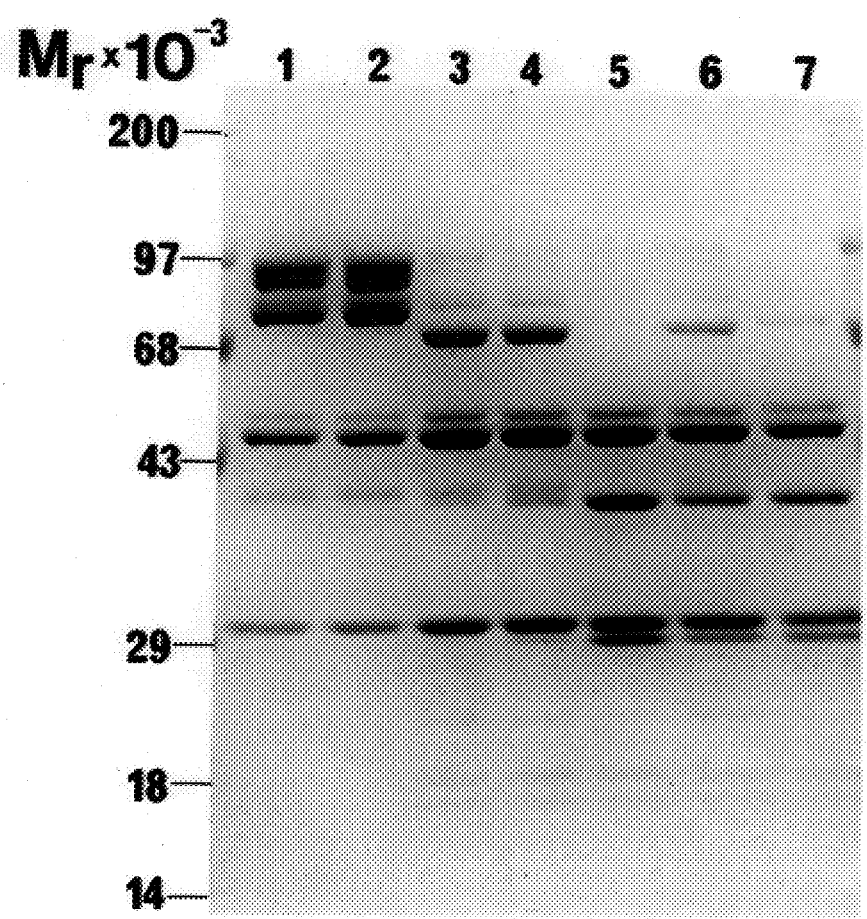
FIG. 3 illustrates the results of the APC digestion of membrane-bound factor Va, as analyzed using linear gradient SDS-PAGE.

FIG. 3—APC Digestion of Membrane-bound Factor Va.

Factor Va (1.23 μM) was incubated with phospholipid vesicles (70 μM) containing various amounts of PC and PS for 5 min at 37° C. APC (62 nM) was then added, and the mixture was incubated for 135 min at 37° C. The reaction was stopped by incubating the mixture with 2% SDS, 2%

β-mercaptoethanol and heating at 90 C. for 5 min. The samples were analyzed by 8–18% linear gradient SDS-PAGE as illustrated. Lane 1, factor Va control, no APC; lane 2, factor Va with PCPS vesicles, no APC; lane 3, factor Va in the presence of APC and in the absence of phospholipid vesicles; lane 4, factor Va in the presence of phospholipid vesicles composed of only PC and APC; lane 5, factor Va incubated with PCPS vesicles and APC; lane 6, factor Va in the presence of PS vesicles and APC; lane 7, following 2-h incubation an aliquot of the sample illustrated in lane 3 was incubated with PCPS vesicles (70 $\mu$M), and further incubation was allowed to proceed 15 min at 37° C. The positions of the molecular weight markers are indicated on the left hand side of the Figure.

Figure 4A:
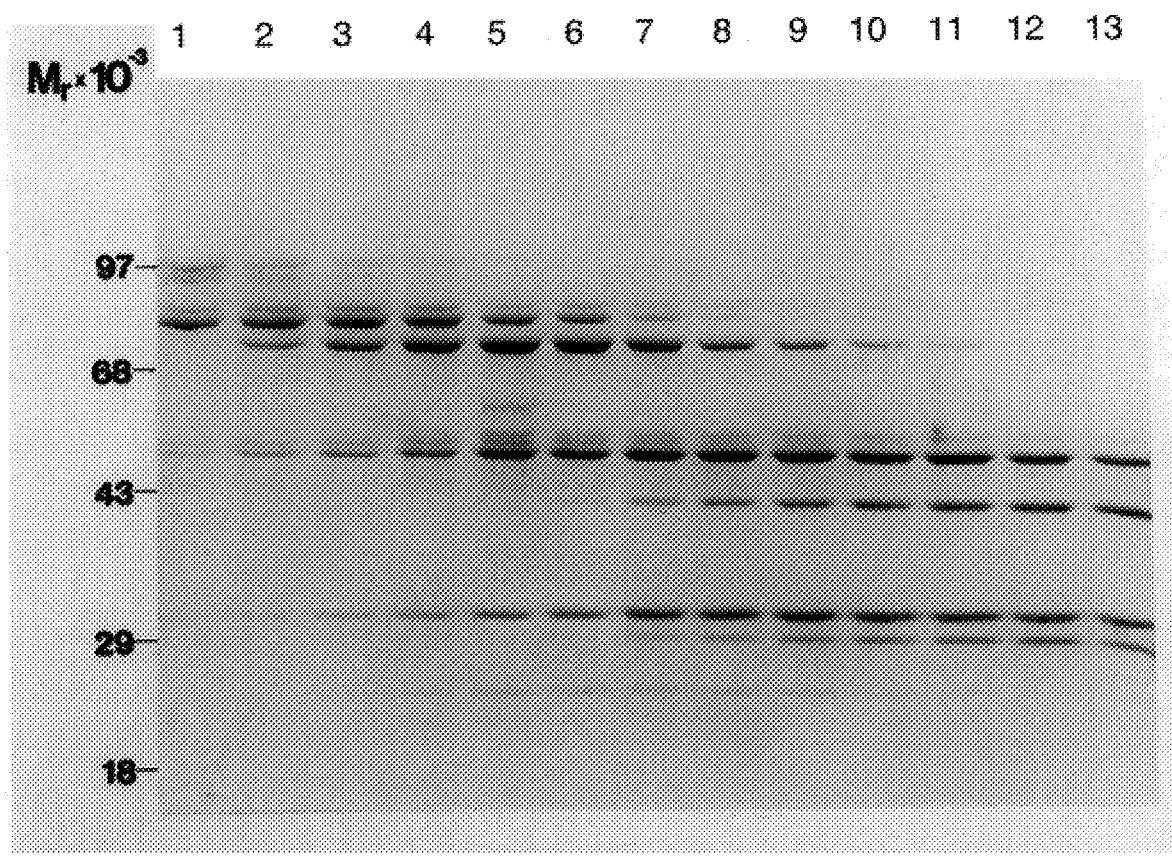
FIG. 4 illustrates the inactivation of factor Va and the correlation thereof with cleavage of the $M_r$ 70,000 fragment of the heavy chain.
Figure 4B:
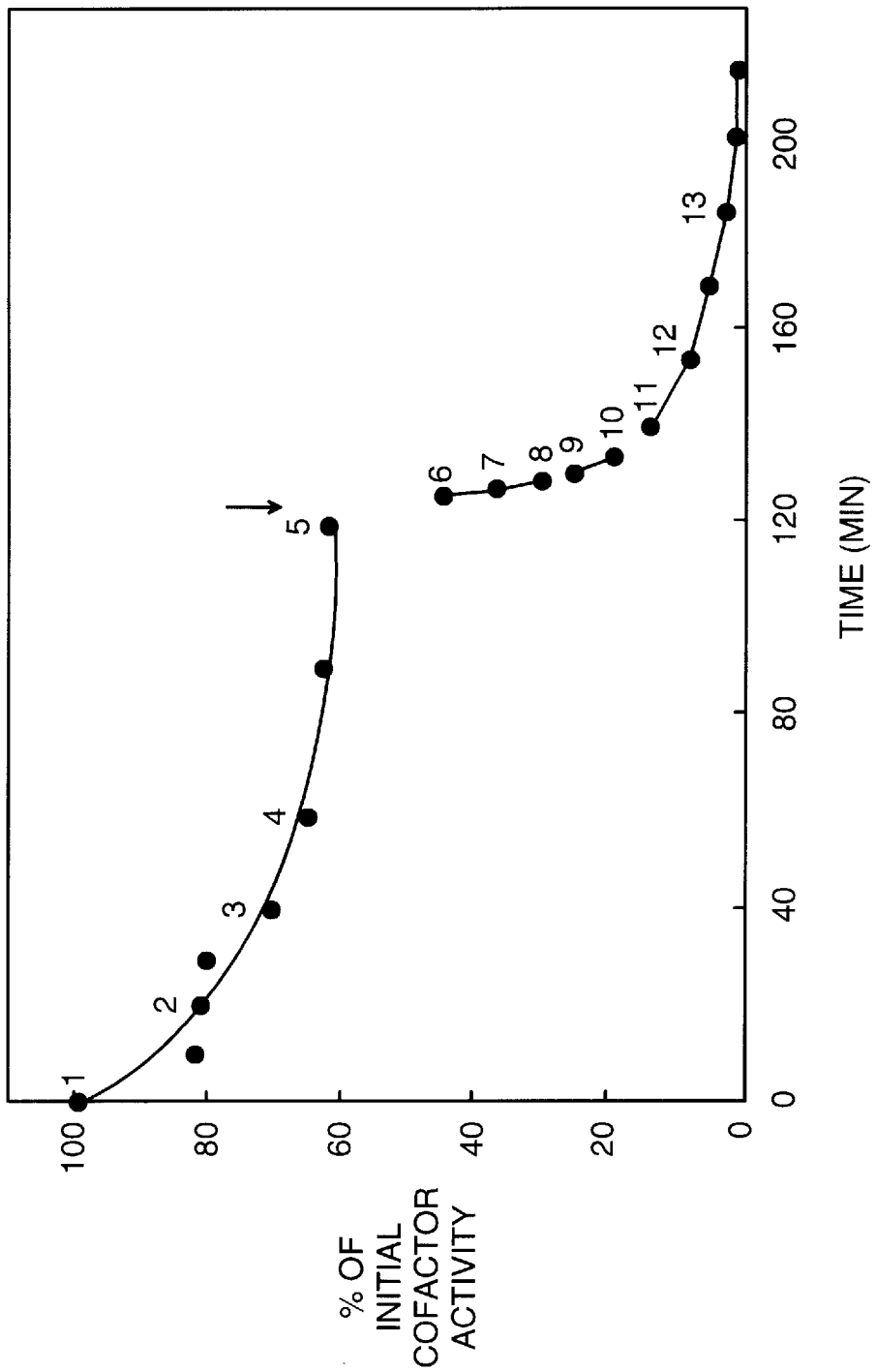

FIG. 4—Inactivation of Factor Va Correlates with Cleavage of the $M_r$ 70,000 Fragment of the Heavy Chain.

Factor Va (400 nM) was incubated with APC (20 nM). At selected time intervals aliquots were mixed with 2% SDS, 2% β-mercaptoethanol, heated for 5 min at 90° C., and analyzed by SDS-PAGE (panel A). At the same time intervals another aliquot of the mixture was assessed for cofactor activity as described below in the Examples (panel B). Following a 2-h incubation, PCPS vesicles were added to the mixture (30 $\mu$M final concentration), and incubation was allowed to proceed for 90 additional min. Panel A, SDS-PAGE analysis (5–15% linear gradient gel) stained with Coomassie Blue. Lane 1, factor Va control, no APC; lanes 2–5, factor Va and APC in the absence of PCPS vesicles at 20 min, 40 min, 1 h, and 2 h. Following a 125-min incubation at 37° C. with APC, PCPS vesicles were added to the mixture. Lanes 6–13 depict aliquots withdrawn at 30 s and 2, 4, 6, 10, 15, and 30 min and 1 hour after the addition of the PCPS vesicles. The positions of the molecular weight markers are indicated on the left.

Panel B, illustrates factor Va cofactor activity. The results are expressed as percent of initial cofactor activity as a function of time before and after the addition of PCPS vesicles. The arrow indicates the moment of the addition of the PCPS vesicles (125 min). The numbers 1–13 in panel B depict samples that were also analyzed by SDS-PAGE in panel A (corresponding to lanes 1–13).

Figure 5:
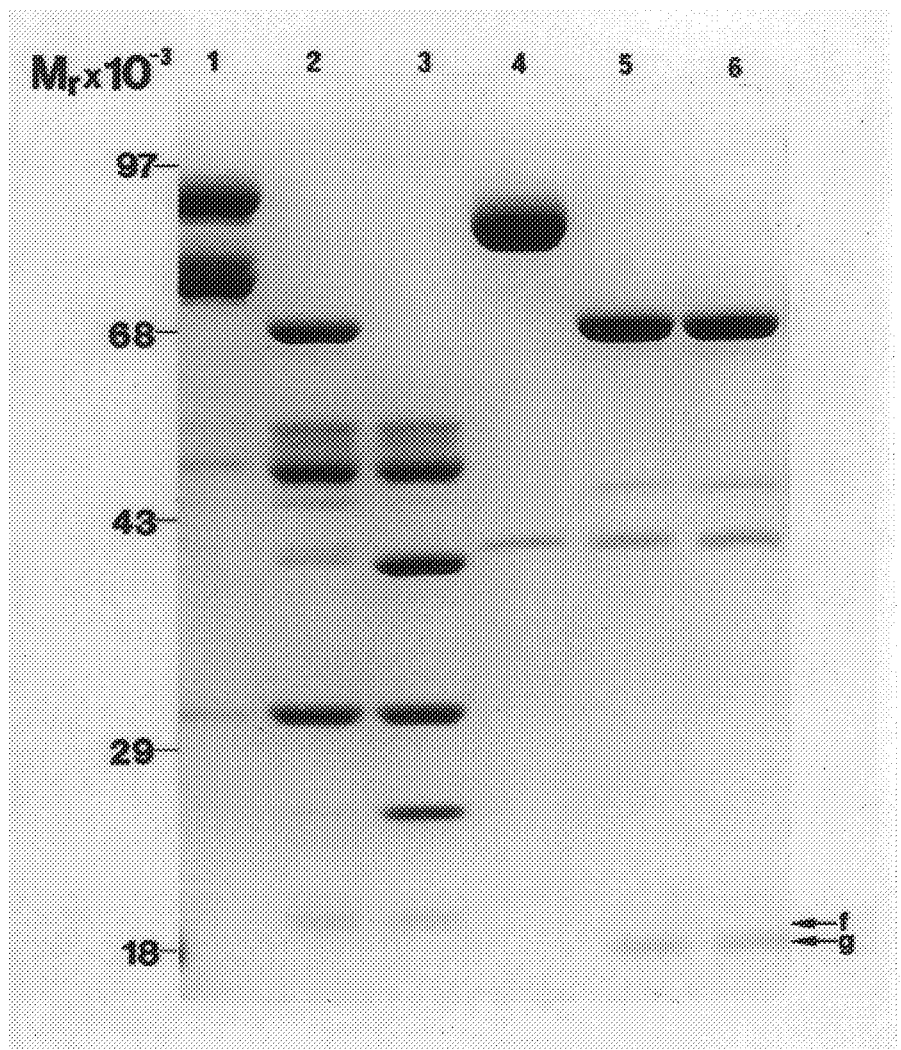
FIG. 5 illustrates the results of the phospholipid dependent cleavage of the $M_r$ 70,000 fragment of the factor Va heavy chain by APC, as analyzed using linear gradient SDS-PAGE.

FIG. 5. Phospholipid Dependent Cleavage of the $M_r$ 70,000 Fragment of the Factor Va Heavy Chain.

Factor Va (3 $\mu$M) and factor Va heavy chain (H90, 3 $\mu$M) were incubated for 5 min at 37° C. with PCPS vesicles (200 $\mu$M). APC was added at 150 nM, and the reaction mixture was further incubated for 3 h at 37° C. Following incubation with 2% SDS the sample was heated for 5 min at 90° C. and analyzed as illustrated on a 5–15% linear gradient SDS-PAGE gel stained with Coomassie Blue. Lane 1, factor Va control, no APC; lane 2, factor Va in the absence of PCPS vesicles and in the presence of APC; lane 3, membrane-bound factor Va in the presence of APC; lane 4, factor Va heavy chain (H90), no APC; lane 5, H90 in the presence of APC; lane 6, H90 in the presence of PCPS and APC. The positions of the molecular weight markers are indicated on the left. f and g indicate the positions of the proteolytic fragments deriving after cleavage of H94 (f) or H90 (g) by APC at Arg$^{505}$ and contianing the COOH-terminal part of the heavy chain (the positions of these fragments within factor Va heavy chain are illustrated in FIG. 6, panel C).

Figure 6A:
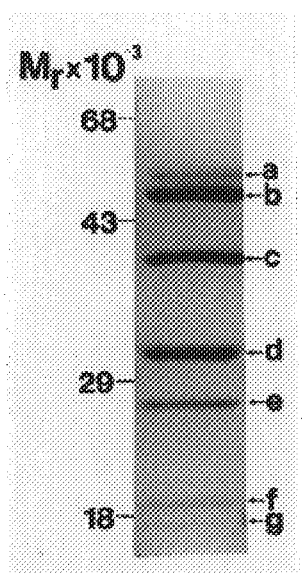
FIG. 6, in panels A (unlettered), B and C, provide identification of the proteolytic cleavages of the factor Va molecule by APC. Panel A is an SDS-PAGE analysis, stained with Coomassie Blue; Panel B illustrates the $NH_2$-terminal sequence of the fragments a–g shown in Panel A; Panel C depicts a schematic representation of the cleavages performed in the factor Va molecule by APC in the presence of PCPS vesicles.

FIG. 6. Identification of the Proteolytic Cleavages of the Factor Va Molecule by APC.

Factor Va (1.36 $\mu$M) was incubated with PCPS vesicles (100 $\mu$M) for 5 min at 37° C. APC (68 nM) was then added, and the mixture was incubated for 3 h at 37° C. The reaction was stopped by the addition of 2% SDS, 2% β-mercaptoethanol, and the mixture was heated for 5 min at 90° C. Approximately 50 $\mu$g of total factor Va digest was analyzed as illustrated in duplicate by 8–18% linear gradient SDS-PAGE. After electrophoresis, the proteins were transferred to a polyvinylidene difluoride membrane following the procedure described below in the Examples. $NH_2$-terminal sequencing was performed on each fragment. Panel A illustrates the Coomassie Blue-stained SDS-PAGE analysis (1–18% linear gradient) of the fragments derived after APC cleavage of membrane-bound factor Va. The positions of the molecular weight markers are indicated on the left. The letters a–g depict bovine factor Va fragments. Panel B illustrates the $NH_2$-terminal sequence of the fragments a–g shown in panel A. The numbers in parentheses indicate pmol of amino acid at the given cycle. NQ, not quantitated. Panel C depicts a schematic representation of the cleavages performed in the factor Va molecule by APC in the presence of PCPS vesicles. The fragments were positioned after comparison of the $NH_2$-terminal sequence found in Panel B with the amino acid sequence derived from the bovine CDNA sequence (9). The factor Va heavy chain (residues 1–713) is composed of two A domains (A1-A2) associated through a connecting region (amino acids 303–319). The COOH-terminal part of the heavy chain contains a cluster of acidic amino acids (denoted by the (dashes)) and Ser$^{690}$ which has been shown to be phosphorylated by a platelet kinase (21). The light chain of the cofactor (amino acids 1537–2183) includes one A and two C domains (A3-C1-C2). The positions of factor Va heavy and light chain degradation products after proteolytic degradation of the membrane-bound cofactor by APC are indicated on the right panel A and in panel C as follows: a, $M_r$ 48,000 fragment; b, $M_r$ 46,000 fragment; c, $M_r$ 40,000 fragment (A1 domain, amino acids 1–306); d, $M_r$ 30,000 fragment ($NH_2$-terminal part of the light chain residues 1537–1752); e, $M_r$ 28,000 fragment ($NH_2$-terminal portion of the A2 domain plus connecting region, amino acids 307–505); f, $M_r$ 20,000 (COOH-terminal part of the A2 domain, residues 506–661); g, $M_r$ 16,000 fragment. The small dashed arrows denoted by 1, 2 and 3 represent cleavages of the heavy and light chain by unidentified proteases. 1 is cleavage at the COOH-terminal part of the heavy chain, which results in the formation of H90 (34); this cleavage has been already reported to occur in platelet-bound factor Va (47). 2 and 3 represent two cleavages that must occur at the COOH-terminal end of the light chain since fragments a and b, which differ in relative migration by approximately 2,000, have the same $NH_2$-terminal sequence, and Cys$^{2021}$ forms a disulfide bond with Cys$^{2180}$ (63). However, the light chain of factor Va also contains four potential glycosylation sites (i.e., Asn$^{1662}$, Asn$^{1811}$, Asn$^{1969}$, and Asn$^{2168}$) (9). It is also possible that the difference between the two light chains species is caused by differences in glycosylation.

Figure 7A:
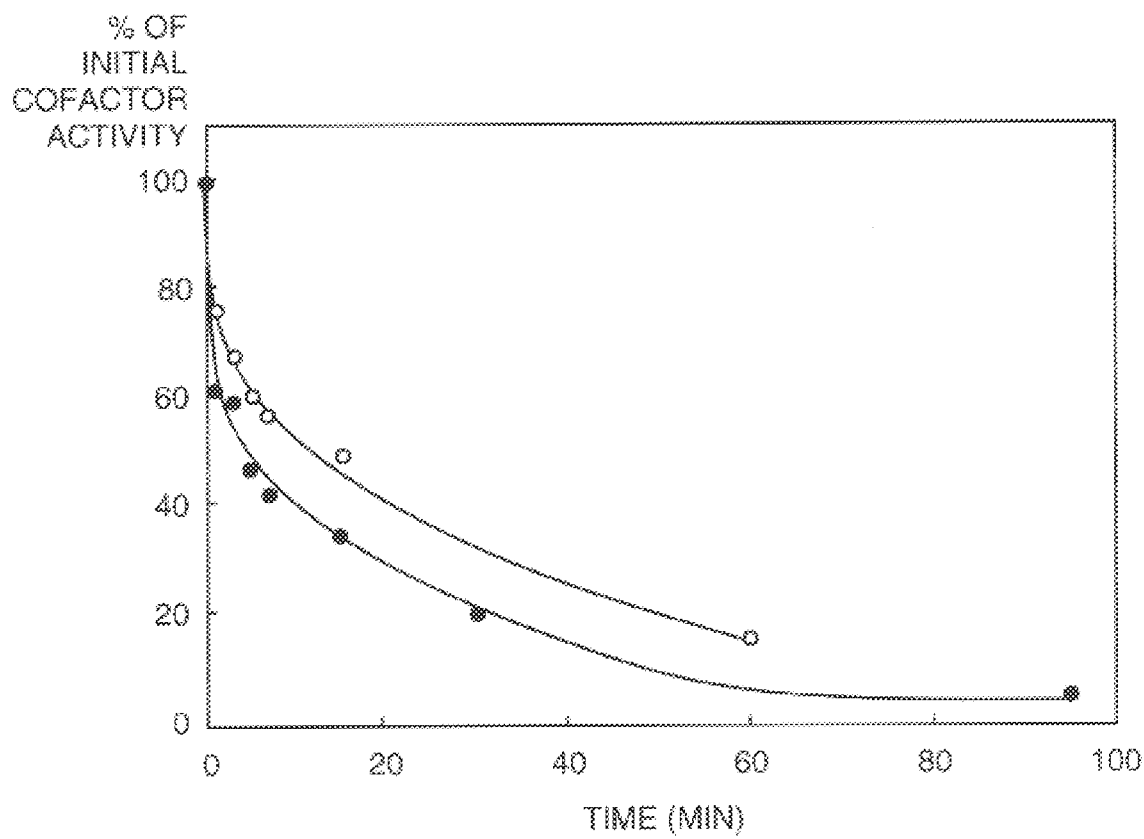
FIG. 7 illustrates the cofactor activity of factor Xa-treated factor Va. In the inset thereof, there is provided an SDS-PAGE depiction of these data.
Figure 7B:
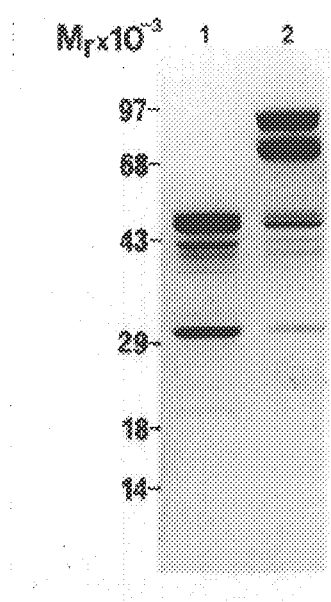

FIG. 7. Cofactor Activity of Factor Xa-treated Factor Va.

Factor Va was treated with factor Xa, and the resulting cofactor was immunopurified and assessed for cofactor activity as described below in the Examples. The initial rates of thrombin formation were calculated and plotted as percent of initial cofactor activity as a function of time after adding APC. In the Figure, Factor Va$_{Xa}$ in the presence of APC is represented by the filled circles; the open circles represent factor Va$_{37C}$. The insert shows an 8–18% SDS-PAGE, which depicts the starting material. Lane 1, factor Va after a 48-h incubation at 37° C. with factor Xa (factor Va$_{Xa}$); lane 2, factor Va after a 48-h incubation at 37° C. in the absence of factor Xa (factor Va$_{37C}$). The positions of the molecular weight markers are indicated on the left.

Figure 8A:
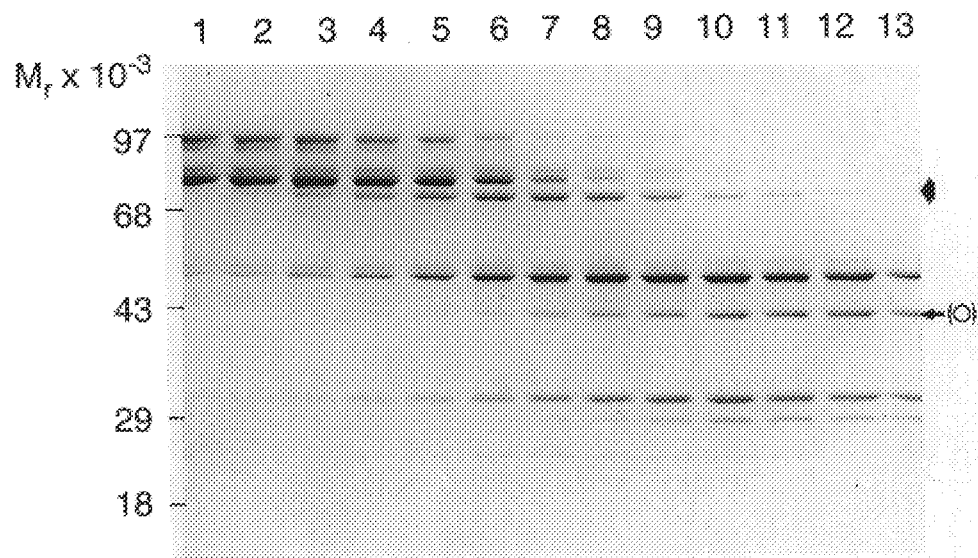
FIG. 8, in panels A, B, and C, illustrates the acceleration of factor Va proteolysis by APC in the presence of protein S. Panels A and B are each Coomassie Blue stained SDS-PAGE analyseis, and Panel C is an analysis of these data by scanning densitometry.
Figure 8B:
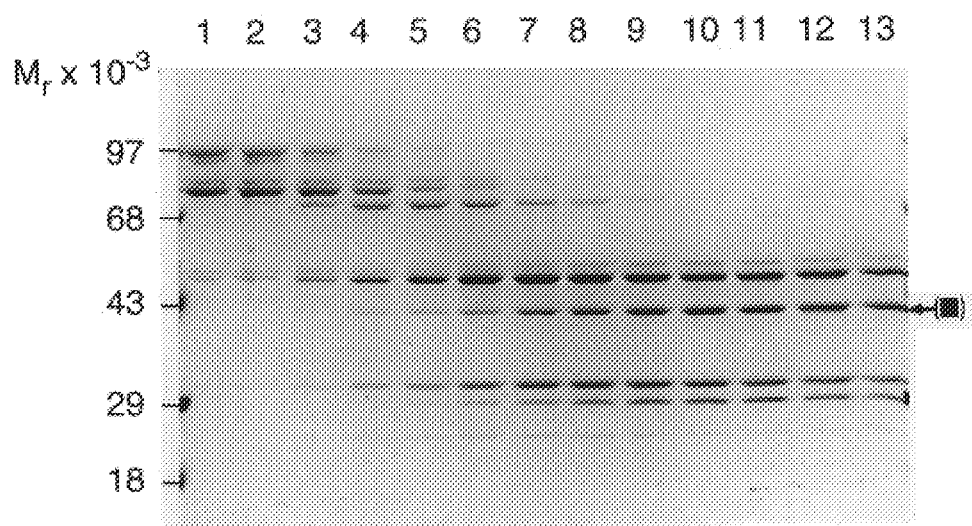
Figure 8C:
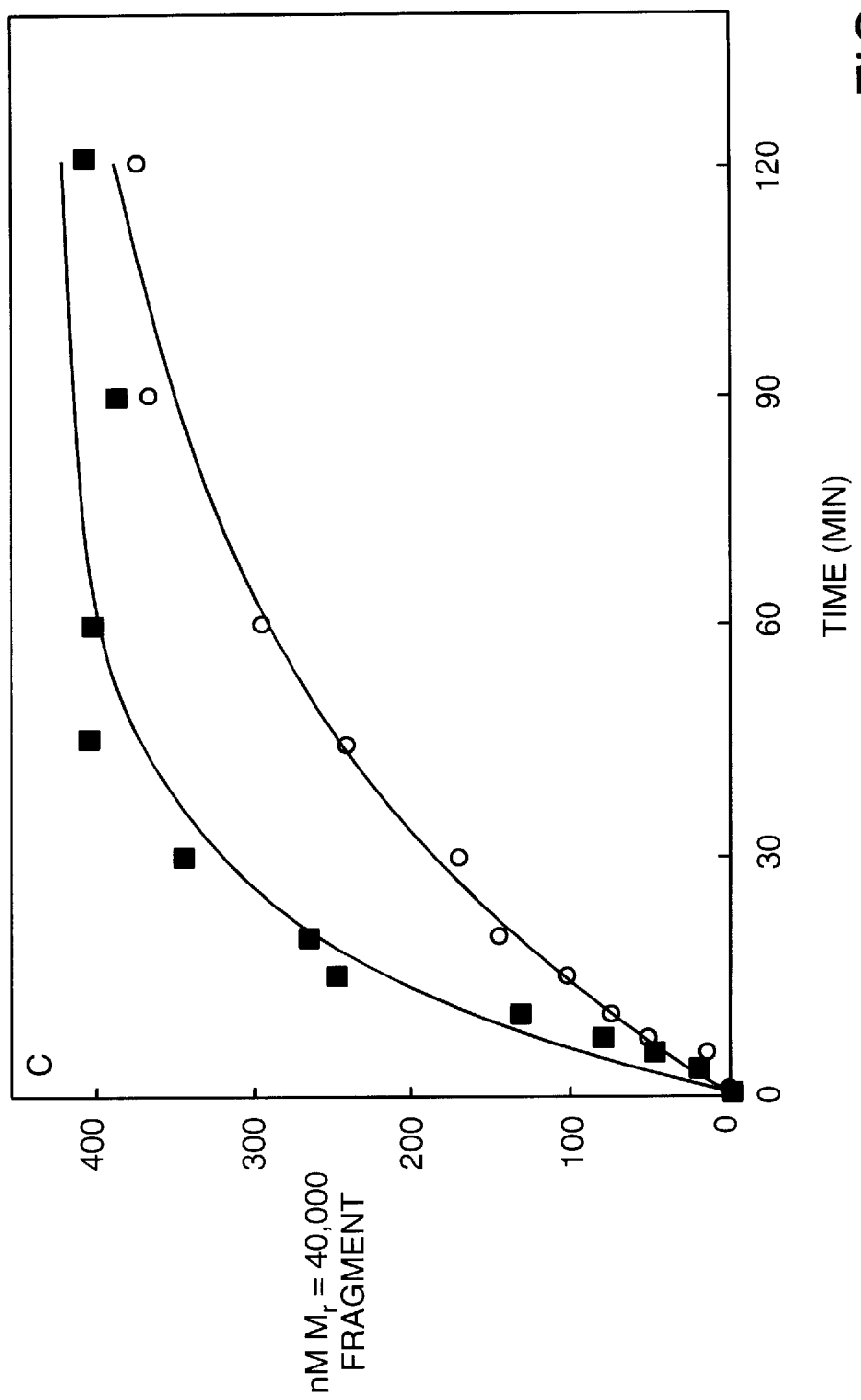

FIG. 8. Acceleration of Factor Va Proteolysis by APC in the Presence of Protein S.

Factor Va was digested with APC in the presence and absence of protein S as described below in the Examples. At various time intervals samples were removed and prepared for SDS-PAGE. As illustrated in this Figure, Panel A is the Coomassie Blue-stained SDS-PAGE (5–15% linear gradient) showing factor Va digested with APC in the presence of PCPS vesicles in the absence of protein S (the same samples were analyzed for cofactor activity). Panel B is the SDS-PAGE (5–15%, linear gradient) stained with Coomassie Blue, showing membrane-bound factor Va proteolysis by APC in the presence of 20 nM protein S. Lane 1, factor Va control, no APC; lanes 2–13 depict factor Va and APC at 1, 3, 5, 7, 10, 15, 20, 30, 45, 60, 90 and 120 min. The positions of the molecular weight markers are indicated on the left of panels A and B. The arrows at the right of panels A (open circle) and B (filled square) indicate the appearance of the $M_r$ 40,000 fragment deriving from the heavy chain of the cofactor after cleavage at $Arg^{306}$ and $Arg^{505}$ of the membrane-bound cofactor by APC alone (nM, open circles) or by APC (4 nM) and protein S (20 nM, filled squares) and analyzed by scanning densitometry in panel C. The arrowhead at the right of panel A shows residual amounts of $M_r$ 70,000 fragment remaining after a 2-h digestion.

Figure 9:
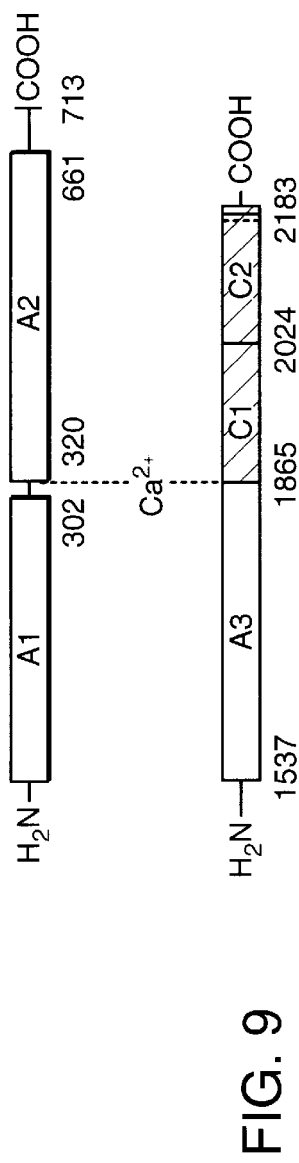
FIG. 9 is a schematic representation of the pathways for bovine factor Va inactivation by APC.
Figure 9:
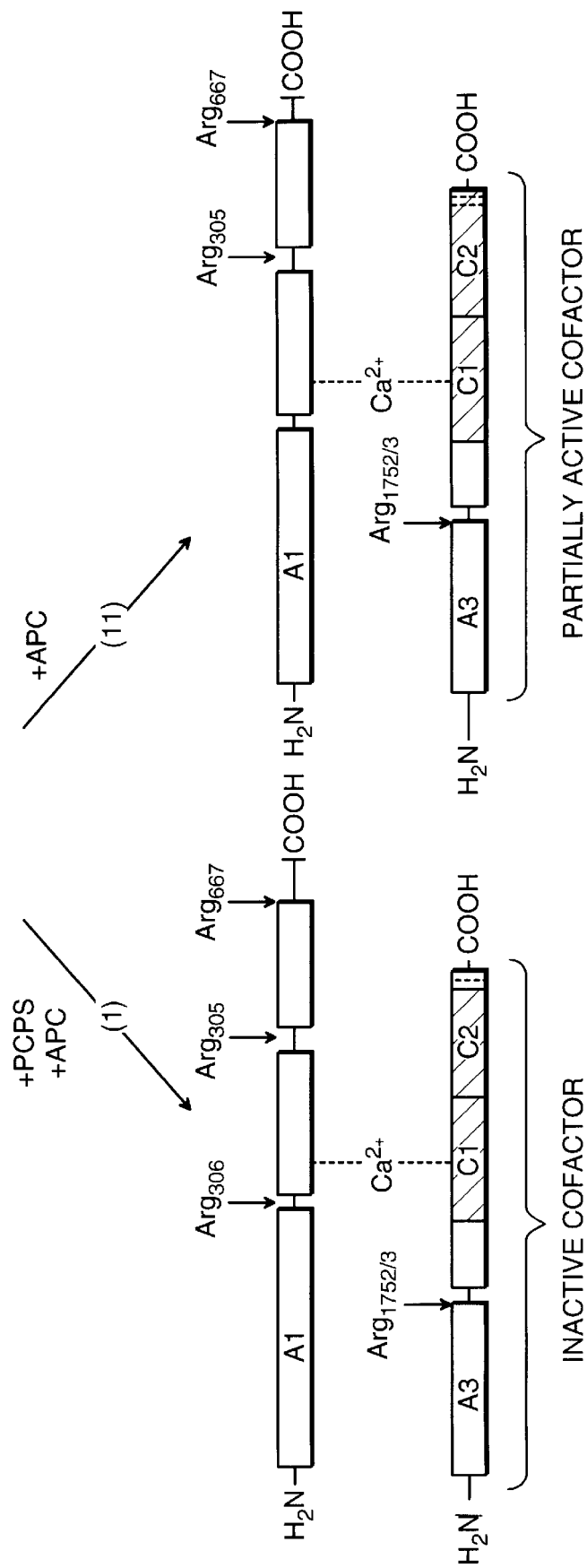

FIG. 9. Schematic Representation of the Pathways for Bovine Factor Va Inactivation by APC.

The domain structure of the cofactor's heavy and light chain is detailed in the legend of FIG. 6. APC cleaves the heavy chain of membrane-bound factor Va at three positions: $Arg^{306}$, $Arg^{505}$, and $Arg^{662}$ (pathway I) and the resulting cofactor is completely inactive. The rate of cleavage of the cofactor by APC at these positions is enhanced in the presence of protein S. APC catalyzes the cleavage of two peptide bonds in factor Va heavy chain in the absence of phospholipid (i.e. $Arg^{505}$, and $Arg^{662}$) to yield a partially active cofactor (pathway II). Protein S has no effect on the rate of these cleavages in the absence of a phospholipid surface. In the presence or absence of phospholipid vesicles APC cleaves the light chain of the cofactor at $Arg^{1752}$ and $Arg^{1753}$.

Proteolytic Alterations of the Factor Va Molecule During Inactivation by APC

Factor Va incubated in the absence or presence of phospholipid vesicles had similar initial cofactor activity (728 nM $IIa \cdot min^{-1} \cdot nM^{-1}$ and 708 nM $IIa \cdot min^{-1} \cdot nM^{-1}$, respectively). APC cleaves membrane-bound factor Va heavy and light chains (FIG. 1, panels A and C) to generate fragments of $M_r$ 70,000, 46,000/48,000, 40,000, 30,000, 28,000, and 20,000 (FIG. 1, panel A, lanes 1–13). The disappearance of the $M_r$ 70,000 fragment is correlated with the appearance of $M_r$ 40,000 and 28,000 fragments (FIG. 1, panels A and E) and the loss of more than 80% of the initial cofactor activity FIG. 2, (filled circles). The disappearance of the $M_r$ 70,000 fragment (after 15 min) corresponds to the loss of approximately 85% of the factor Va cofactor activity (FIG. 2). In the absence of membranes, bovine factor Va heavy chain is cleaved by APC at $Arg^{505}$ and $Arg^{662}$ generating fragments of $M_r$ 70,000, 20,000, and a $M_r$ 4,000 peptide (20, 21). In the absence of a membrane surface APC cleaves the light chain of the bovine cofactor at $Arg^{1752}$ resulting in $M_r$ 30,000 and 46, 000/48,000 fragments (FIG. 1, panel B, lanes 1–13; Ref. 20). The resulting factor Va displays 60% of its initial cofactor activity (FIG. 2, open circles). In the absence of PCPS vesicles the $M_r$ 70,000 fragment is not cleaved by APC during a 2-h incubation period (FIG. 1, panels B and F). In contrast, in the presence of phospholipid there is an increase in the $M_r$ 40,000 and 28,000 fragments (FIG. 1, panel E), which at 30 min is associated with the loss of more than 97% of the initial cofactor activity of membrane-bound factor Va (FIG. 2). These observations suggest that the complete disappearance of the $M_r$ 70,000 fragment can be correlated with the total loss of the cofactor activity. In the presence of phospholipid vesicles the heavy and light chains of the cofactor are cleaved faster than the factor Va subunits in the absence of a lipid bilayer; however, in either case the light chain of the cofactor is more resistant to APC proteolysis than the heavy chain (FIG. 1, panels C and D).

Since prolonged incubation of factor Va with APC in the absence of PCPS vesicles did not totally eliminate cofactor activity, the properties of factor Va treated with APC (plus or minus PCPS vesicles) after a 24-h incubation at 37° C. were compared. Following a 24-h incubation at 37° C. the control factor Va retains approximately 80% or its initial cofactor activity. After a 24-h incubation at 37° C. with APC and PCPS membranes, the product possesses no cofactor activity. In contrast, in the absence of PCPS vesicles after a 24-h incubation at 37° C. with the APC factor Va retains approximately 30% of its initial cofactor activity. Comparative electrphoretic analysis of APC-treated factor Va seen in the absence of a lipid surface can be attributed to the presence of the $M_r$ 70,000 fragment.

The overall data suggest that the complete loss of activity of the cofactor is best correlated with the membrane-dependent cleavage of the $M_r$ 70,000 fragment of the heavy chain of the bovine cofactor (residues 1–505) resulting in the appearance of fragments of $M_r$ 40,000 and 28,000.

Lipid Dependence of the Cleavage of the $M_r$ 70,000 Fragment of the Heavy Chain To ascertain whether cleavage of the $M_r$ 70,000 fragment by APC is dependent upon the binding of the light chain of factor Va to PCPS vesicles the cleavage pattern of the cofactor by APC in the absence of a lipid surface or in the presence of phospholipid vesicles composed of various weight percent amounts of PC and PS was evaluated. No contaminating proteolytic activity was detected in the buffer or the phospholipid vesicle controls FIG. 3, lanes 1 and 2). With APC, in the absence of a lipid surface, no cleavage of the $M_r$ 70,000 fragment is observed during a 2-h incubation period (FIG. 3, lane 3). After a 2-h incubation, a sample of the mixture shown in FIG. 3, lane 3, was incubated with PCPS vesicles of 15 additional min and analyzed by SDS-PAGE (FIG. 3, lane 7). The rapid disappearance of the $M_r$ 70,000 fragment still remaining after a 2-h incubation of the cofactor with APC in the absence of lipids is correlated with the appearance of fragments of $M_r$ 40,000 and 28,000. In the presence of phospholipid vesicles containing only PC, small amounts of $M_r$ 40,000 and 28,000 are detected, suggesting a weak interaction of factor Va with phospholipid vesicles containing only neutral phospholipid and a slow cleavage of $M_r$ 70,000 fragment (FIG. 3, lane 4). In the presence of PCPS vesicles or phospholipid vesicles containing only PS, significant amounts of fragments of $M_r$ 40,000 and 28,000 are detected (FIG. 3, lanes 5 and 6). However, a comparison of lane 5 with lane 6 suggests that cleavage of the $M_r$ 70,000 fragment occurs faster when the cofactor is bound to the PCPS vesicles (FIG. 3, lane 5). Collectively, these data suggest, as described recently, that factor Va interacts with both 100% PC and 100% PS vesicles (41,42).

In an attempt to verify that cleavage of the $M_r$ 70,000 fragment, which is lipid-dependent, is required for cofactor inactivation, a factor Va solution (initial cofactor activity of 675 nM $IIa \cdot min^{-1} \cdot nM^{-1}$) was incubated for 2 hours with APC in the absence of phospholipid vesicles. Under these conditions the cofactor retains 60% of its initial cofactor activity (FIG. 4, panel B). Following APC digestion, PCPS vesicles were added (FIG. 4, panel B, arrow). A rapid decrease in the factor Va cofactor activity was observed. The rapid loss of the cofactor activity of the APC-treated cofactor in the presence of a membrane surface coincided with the fast disappearance of the $M_r$ 70,000 fragment and the appearance of fragments of $M_r$ 40,000 and 28,000 (FIG. 4, panel A, lanes 6–13). No cofactor activity and no $M_r$ 70,000 fragment were observed after incubation of PCPS vesicles with the APC-treated cofactor (FIG. 4, panel A, lane 13, and FIG. 4, panel B).

Collectively these data demonstrate that, 1) the $M_r$ 70,000 fragment of the heavy chain provides factor Va cofactor activity in association with the light chain or its degradation products; 2) complete inactivation requires PCPS vesicles; 3) upon binding to an appropriate lipid surface, factor Va displays a new cleavage site for APC, on the $M_r$ 70,000 fragment resulting in fragments with $M_r$ 40,000 and 28,000.

To determine whether cleavage of the $M_r$ 70,000 fragment of the membrane-bound cofactor is caused by the exposure of a new proteolytic inactivating site for APC on the factor Va molecule or by alterations of the properties of APC bound to a phospholipid surface, the isolated factor Va heavy chain, lacking the COOH-terminal portion (H90) was digested with APC in the presence and absence of PCPS vesicles. No difference in the cleavage pattern of the heavy chain of the cofactor (H90) was observed in the presence or absence of PCPS vesicles (FIG. 5, lanes 5 and 6), whereas for intact factor Va, which possesses the lipid binding site(s) on the light chain (41-46), the lipid-dependent cleavage of the $M_r$ 70,000 fragment is observed (FIG. 5, lane 3). These data demonstrate that both the light chain of the cofactor and phospholipid are required for the cleavage of the $M_r$ 70,000 fragment of the heavy chain by APC.

Identification of the APC Inactivating Cleavage Sites

All fragments (denoted by a–g in FIG. 6, panel A) were analyzed for $NH_2$-terminal sequence (FIG. 6, panel B), compared with the amino acid sequence derived from the cDNA of the bovine molecule (9), and positioned accordingly in the structure of the heavy and light chains of the cofactor (FIG. 6, panel C).

Two $NH_2$-terminal sequences were found for the $M_r$ 48,000 fragment (a) as well as for the $M_r$ 46,000 fragment (b) and indicate that APC cleaves the light chain of the membrane-bound cofactor at two positions, $Arg^{1752}$ and $Arg^{1753}$, generating fragments that differ by 1 amino acid at their $NH_2$ termini (i.e., RASSEVKNSH SEQUENCE I.D. NO.1 and ASSEVKNSH, SEQUENCE I.D. NO.2 respectively). Cleavage of the light chain at $Arg^{1752}$ has been shown previously to occur when the cofactor was incubated with APC in the absence of phospholipid vesicles (20). Experiments that examined APC cleavage of factor Va in the absence of lipid confirmed those results (Table I). However, both fragments of $M_r$ 48,000 and $M_4$ 46,000 showed the same heterogeneity at their $NH_2$ termini (Table I). Thus, factor Va exposes on the light chain two APC cleavage sites (i.e., $Arg^{1752}$ and $Arg^{1753}$).

The $M_r$ 40,000 fragment (c) generated by cleavage of the $M_r$ 40,000 fragment (c) generated by cleavage of the $M_r$ 70,000 fragment of the heavy chain is the $NH_2$-terminal portion of the heavy chain of factor Va (FIG. 6, panel B). The $M_r$ 30,000 fragment (d) is the $NH_2$-terminal part of the bovine factor Va light chain (9). The $NH_2$-terminal sequence of the $M_r$ 28,000 fragment (e) which is complementary to the $M_r$ 40,000 fragment (c) begins at residue 307 and thus represents cleavage of the heavy chain by APC at $Arg^{306}$ (FIG. 6, panels B and C).

At residue 321 two distinct phenylthiohydantoins were detected (Arg and Phe) with similar yields (10.11 and 11.5 pmol, respectively). Since the factor Va preparation was derived from blood collected from 10 cows (32), it is likely that polymorphism at residue 321 may be common.

Fragments f and g both match with a portion of bovine factor V starting at amino acid residue 506 (FIG. 6, panels B and C). Control experiments performed in the absence of lipid demonstrated that after a 3-hour incubation with APC both fragments of $M_r$ 24,000 ($f_0$) and $M_r$ 20,000 (f) were detected (Table I). In contrast, no $M_r$ 24,000 fragment was detected after 3 hours in the presence of PCPS vesicles. Thus, cleavage at both $Arg^{505}$ and $Arg^{662}$ is accelerated in the presence of a membrane surface.

Most bovine factor Va preparations present heterogeneity at the COOH-terminal end of the heavy chain of the cofactor (34, 47). The present data suggest that the cleavage by an unidentified protease is distinct from APC cleavage at $Arg^{662}$ (21) and occurs in the A2 domain since fragment g has a lower molecular weight than fragment f ($M_r$ 20,000 for fragment f and $M_r$ 16,000 for fragment g; FIG. 5). The difference between fragments f and g is obvious when comparing APC cleavage of factor Va containing a $M_r$ 94,000 heavy chain with APC cleavage of the isolated H90 (FIG. 5, lanes 2, 3, 5, and 6).

TABLE I

Sequence of $NH_2$-terminal amino acid residues of the fragments deriving upon APC cleavage of factor Va in the absence of PCPS vesicles
The number in parentheses indicates pmol at the given cycle.

| Cycle no. | $M_g$ = 48,000 (a)[a] | $M_g$ = 46,000 (b) | $M_g$ = 70,000 (c + e) | $M_g$ = 30,000 (d) | $M_g$ = 24,000 ($f_0$)[b] | $M_g$ = 20,000 (f) |
|---|---|---|---|---|---|---|
| 1 | R(1.10)/A(1.0) | R(10.87)/A(5.10) | A(11.35) | S(9.20) | G(2.30) | G(17.54) |
| 2 | A(1.31)/— | A(12.52)/— | K(2.27) | N (14.91) | I(1.69) | I(11.89) |
| 3 | S(0.60)/— | S(2.13)/S(1.00) | L(9.66) | T(8.78) | Q(1.92) | Q(13.12) |
| 4 | S(0.20)/E(0.20) | S(1.70)/E(1.21) | R(7.11) | G(9.78) | R(1.18) | R(8.23) |
| 5 | E(0.86)/V(0.20) | E(5.09)/V(0.70) | Q(7.08) | N(10.96) | A(1.34) | A(10.42) |
| 6 | V(0.63)/K(0.10) | V(3.90)/K(0.60) | F(6.53) | R(8.46) | A(1.94) | A(12.18) |
| 7 | K(0.15)/N(0.30) | K(1.80)/N(1.39) | Y(4.40) | K(2.69) | D(1.89) | D(7.80) |
| 8 | N(0.84)/S(0.20) | N(4.14)/— | V(4.73) | Y(4.69) | I(0.79) | I(7.01) |
| 9 | S(0.30)/— | S(0.94)/H(0.50) | A(4.60) | Y(5.50) | E(0.37) | E(6.06) |
| 10 | H(0.19)/— | H(0.78)/E(0.20) | A(5.79) | Y(4.72) | Q(0.92) | Q(6.60) |
| 11 | — | E(0.60)/F(0.50) | | | | |
| 12 | F(0.20)/— | F(1.28)/— | | | | |

TABLE I-continued

Sequence of NH$_2$-terminal amino acid residues of the fragments deriving upon APC cleavage of factor Va in the absence of PCPS vesicles
The number in parentheses indicates pmol at the given cycle.

| Cycle no. | M$_g$ = 48,000 (a)[a] | M$_g$ = 46,000 (b) | M$_g$ = 70,000 (c + e) | M$_g$ = 30,000 (d) | M$_g$ = 24,000 (f$_0$)[b] | M$_g$ = 20,000 (f) |
|---|---|---|---|---|---|---|
| 13 | — | H(1.01)/A(0.40) | | | | |
| 14 | A(0.10)/— | A(1.33)/— | | | | |
| 15 | I(0.08)/— | I(0.78)/N(0.50) | | | | |
| 16 | — | N(1.03)/G(0.80) | | | | |
| 17 | — | G(0.85)/— | | | | |
| 18 | — | M(0.32)/— | | | | |
| 19 | — | I(0.40)/— | | | | |
| 20 | — | Y(0.38)/— | | | | |

Figure 6C:
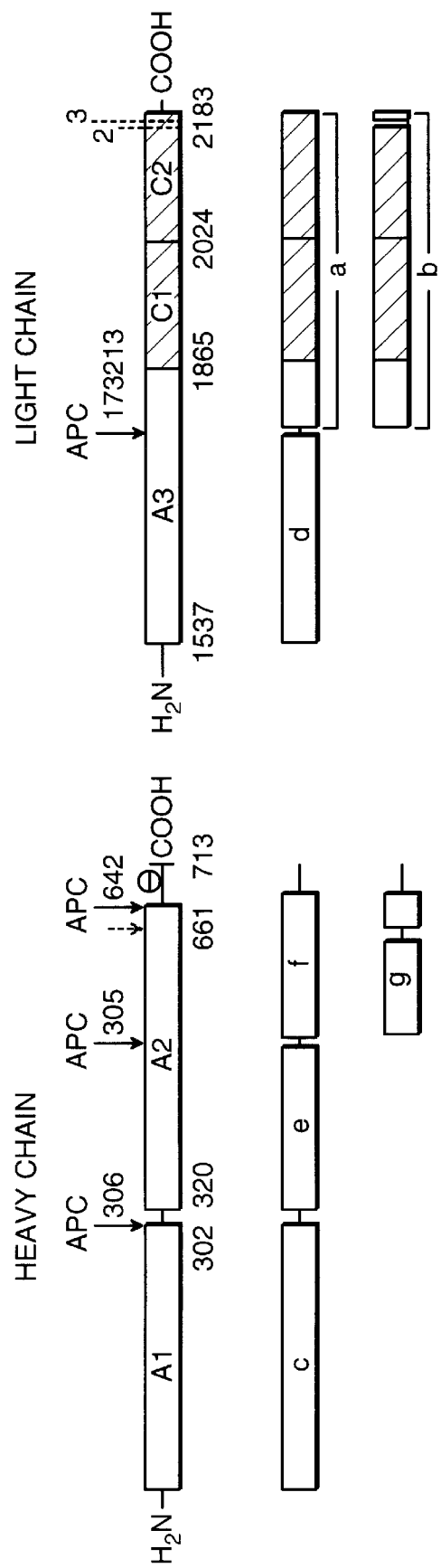

[a] a, b, c, d, e and f represent factor Va fragments after degradation by APC as depicted in FIG. 6C.
[b] f$_0$ denotes the M$_g$ = 24,000 fragment of the heavy chain of factor Va containing amino acids residues (506–713).

Fractionation of APC-inactivated Membrane-bound Factor Va (Va)

To test whether cleavage at Arg$^{306}$, Arg$^{505}$ and Arg$^{662}$ leads to the dissociation of the factor Va molecule, gel filtration and ion exchange chromatography experiments were performed. Gel filtration chromatography of factor Va showed coelution of all of the fragments in the presence of Ca$^{2+}$. In the presence of EDTA the light chain fragments were eluted first in the void volume of the column (bound to the PCPS vesicles) followed by a peak containing the M$_r$ 40,000, 28,000, and 20,000 fragments representing the heavy chain of factor Va. Ion exchange chromatography performed in the presence of EDTA resulted in the coelution of the three fragments representing the heavy chain of the cofactor. These results demonstrate that upon inactivation, the fragmented light and heavy chain remain noncovalently associated through Ca$^{2+}$-dependent interactions and that Ca$^{2+}$-independent interactions are involved in the intra-subunit association. Thus, it can be concluded that upon cleavage by PC at Arg$^{306}$, Arg$^{505}$, and Arg$^{662}$ the A1 domain- and the A2 domain-derived fragments remain associated.

Factor Xa "Protection" of Factor Va

In view of the new membrane-dependent inactivating cleavage site a test was conducted to ascertain whether factor Xa protects factor Va from APC inactivation by binding at or near the APC binding site on the factor Va molecule or if proteolytic action by factor Xa would be sufficient for protection. In the absence as well as in the presence of a phospholipid surface Xa cleaves factor Va at two positions: Arg$^{348}$ and Arg$^{1752}$ (11, 20). The cleavage of the heavy chain at Arg$^{348}$ generates a M$_r$ 56,000 fragment including the NH$_2$-terminal portion of the heavy chain (residues 1–348) and a M$_r$ 45,000 fragment containing the carboxyl-terminal end of the cofactor's heavy chain (amino acid 349–713) (20). The cleavage of the light chain at Arg$^{1752}$ produces the same fragments generated by APC (see FIG. 7, inset).

Following complete digestion of factor Va, factor Xa was immunochemically removed from the solution, and the cleaved cofactor (factor Va$_{Xa}$) was assessed for cofactor activity. Following this treatment, the factor VA$_{Xa}$ solution had an initial cofactor activity of 232 nM IIa·min$^{-1}$·nM$^{-1}$. A control preparation subjected to an identical treatment (in the absence of Factor Xa) demonstrated that factor Va incubated at 37° C. (factor Va$_{37C}$) for 48 h in the absence of factor Xa had an initial cofactor activity of 343 nM IIa.min$^{-}$$_{1}$·nM$^{-1}$. Thus, after all of the manipulations (i.e., incubation of the cofactor at 37° C., for 48-h immunopurification with αBFX-2B and centrifugation) factor Va$_{Xa}$ as well as factor Va$_{37C}$ lost approximately 50% of the initial cofactor activity. No difference was observed between the inactivation rates for factor Va$_{Xa}$ or factor Va$_{37C}$ by APC (FIG. 7). SDS-PAGE analysis of the cleavage products derived upon APC digestion of factor Va$_{37C}$ displayed a similar cleavage pattern, as shown in FIG. 1, panel A. SDS-PAGE analysis of the cleavage products derived from factor Va$_{Xa}$ after APC proteolysis followed by silver staining demonstrated that cleavage of the M$_r$ 56,000 fragment at Arg$^{306}$ occurs simultaneously with the appearance of a M$_r$ 40,000 fragment and the loss in cofactor activity. These data are consistent with the conclusion that the region 307–348 of the cofactor plays a critical role in cofactor function. Altogether these data indicate that the factor Xa protection from APC cleavage requires the binding of factor Xa to factor Va (17) and that cleavage of factor Va by factor Xa is of no consequence for the reaction.

The Contribution of Protein S

Earlier studies demonstrated that protein S exercises its cofactor activity only in the presence of a membrane surface (25). Control experiments performed in the absence of a phospholipid bilayer demonstrates no effect of protein S on the proteolysis and inactivation of factor Va by APC. Inactivation of the cofactor occurs rapidly at a 1:20 enzyme to substrate ratio in the presence of a phospholipid bilayer. Thus, to examine the effect of protein S the enzyme to substrate ratio was 1:100. In the presence of APC (4 nM, protein S (20 nM) increases the factor Va inactivation rate approximately 2-fold as compared with APC alone. SDS-PAGE analysis of the factor Va samples evaluated for cofactor activity demonstrates no new fragments and no effect or protein S on the mechanism of the reaction (FIG. 8, panels A and B). However, in the presence of protein S cleavage of the light and heavy chains and of the M$_r$ 70,000 fragment as well as the appearance of the M$_r$ 40,000 and 28,000 fragments occurred approximately twice faster than in the presence of APC alone (FIG. 8, panel C). The initial rates of the formation of the M$_r$ 40,000 fragment were 1.75 nM·min$^{-1}$·nM$^{-1}$ in the presence of APC alone and 3.25 nM.min$^{-1}$.nM$^{-1}$ in the presence of APC and protein S (FIG. 8, panel C). These data demonstrate that the inactivation of the cofactor which is correlated with cleavage of the heavy chain at Arg$^{306}$, Arg$^{505}$, and Arg$^{662}$ is accelerated in the presence of protein S.

These data demonstrate that membrane-bound factor Va inactivation of APC requires cleavage at Arg$^{306}$, Arg$^{505}$, and Arg$^{662}$ of the heavy chain (FIG. 9). The proteolytic inactivation of membrane-bound factor Va appears to be an ordered and sequential event. The first cleavage occurs at Arg$^{505}$, resulting in Mr 70,000 and 24,000 fragments followed by cleavage at Arg$^{306}$ and Arg$^{662}$. Cleavage at Arg$^{306}$ of the M$_r$ 70,000 fragment results in fragments of M$_r$ 40,000 and 28,000, whereas cleavage at Arg$^{662}$ of the M$_r$ 24,000 generates a M$_r$ 20,000 fragment and a M$_r$ 4,000 peptide (FIG. 9). The essential cleavage for the in activation at Arg$^{306}$ is anionic lipid-dependent. These conclusions are supported by the following evidence. 1) The M$_r$ 70,000 fragment is an intermediate of the inactivation process of membrane-bound factor Va (FIG. 1, panel A and FIG. 4). 2) In the absence of a phospholipid surface cleavage at Arg$^{505}$ occurs and is not sufficient to obliterate factor Va cofactor activity (FIG. 4). 3) The cleaved cofactor at Arg$^{505}$, Arg$^{662}$, and Arg$^{1752}$ in the absence of phospholipid vesicles still interacts with the lipid surface and is cleaved by APC ar Arg 306 (FIG. 3, lane 7, and FIG. 4). These data strongly suggests that the APC cleavage site at Arg$^{505}$ is subjected to fewer constraints and is available to APC. In contrast, the APC site at Arg$^{306}$ is inaccessible to APC. Following binding of factor Va to a phospholipid bilayer, the Arg$^{306}$ site is accessible to APC.

These data demonstrate that cleavage of the cofactor at Arg$^{505}$ and Arg$^{306}$ is accelerated in the presence of a lipid bilayer. These data together with the fact that cleavage at Arg$^{306}$ is anionic lipid-dependent suggest that the binding of the light chain to a membrane surface influences the exposure of the APC cleavage sites on the heavy chain and/or that the catalytic efficiency of APC is influenced by the presence of a phospholipid bilayer. it has been reported that the light chain of the bovine or human cofactor is responsible for its interaction with APC (48,49). It has been also shown that APC-treated factor Va heavy chain and APC-treated factor Va display weaker interaction with prothrombin, factor Xa, or APC in the absence of a phospholipid bilayer (18, 22, 23, 48). However, when factor Va is cleaved by APC in the absence of phospholipid vesicles the cleaved cofactor still retains a significant fraction of its initial activity. These data suggest that in the presence of a phospholipid bilayer the cleaved cofactor still interacts with factor Xa and prothrombin albeit less strongly. Thus, cleavage at Arg$^{505}$ together with the cleavage at Arg$^{662}$ probably generates a cofactor that possesses lower affinity for factor Xa and/or prothrombin than native factor Va. These data also support the fact that even after complete cleavage at Arg$^{505}$, Arg$^{662}$, and Arg$^{1752}$, the fragmented membrane-bound factor Va still inter, acts with APC since a third APC cleavage occurs at Arg$^{306}$ (FIG. 4, lanes 7–13). Thus, it can be concluded that cleavage at Arg$^{306}$, which results in the complete inactivation of factor Va by APC, requires three important steps: 1) cleavage of factor Va at Arg$^{505}$; 2) binding of the cofactor to a membrane surface; and 3) binding of APC to the lipid bilayer and to its specific site on the factor Va light chain.

It is well established that inactivation of the cofactor is correlated with cleavage of the heavy chain and that factor Xa protects factor Va from APC inactivation (16,17,20,50). On the other hand, the heavy chain of the cofactor is involved in the interaction of factor Va with factor Xa and prothrombin (18, 22, 23). Factor Xa cleaves bovine factor Va heavy chain at Arg$^{348}$, and the resulting molecule maintains cofactor activity (20). Factor Va$_{Xa}$ is inactivated by APC at the same rate as the native cofactor (FIG. 7). Furthermore, the M$_r$ 56,000 fragment of the heavy chain of factor Va$_{Xa}$ (residues 1–348) is cleaved at Arg$^{306}$ to give a M$_r$ 40,000 fragment. This cleavage is correlated with the complete loss of the cofactor activity of factor Va$_{Xa}$ no longer possesses cofactor activity, suggesting that the cleaved cofactor no longer interacts with factor Xa and/or prothrombin. Thus, the region containing amino acids 307–348 of the bovine factor Va heavy chain appears to play an essential role in the factor Va cofactor activity and either possesses a binding domain for factor Xa or prothrombin or dictates conformational constraints that are necessary for factor Va cofactor activity. Furthermore, these data demonstrate that factor Xa binding to factor Va and not simply cleavage is essential for the protection of the cofactor by APC inactivation.

The inactivation cleavage pattern of bovine factor Va by APC in the presence of phospholipid is similar to the cleavage pattern obtained after proteolytic action of APC on human factor VIIIa (51-53). It has been clearly established that inactivation of factor VIIIa occurs after cleavage of the cofactor at Arg$^{336}$ (between the A1 and A2 domains) and at Arg$^{562}$ (within the A2 domain) (52). These cleavages result in the faster dissociation of the A2 subunit of factor VIIIa, which is necessary for cofactor activity (54). The order of the cleavages proposed is Arg$^{562}$ followed by Arg$^{336}$ (52). Thus, upon cleavage of the factor VIIIa molecule by APC the A2 domain is released in two fragments (A2$^N$ and A2$^C$) (52). However, it should be noted that the A2 domain dissociates from the A1/A3-C1-C2 dimer in the absence of APC, resulting in an inactive cofactor (55). The gel filtration and ion exchange chromatography performed with bovine factor Va demonstrate a significant difference between the human factor VIIIa and bovine factor Va molecules. In the bovine factor Va molecule, the M$_r$ 40,000 (A1 domain, amino acids 1–306) is associated with the M$_r$ 28,000 and 20,000 fragments (amino acids 307–505 and 506–661, respectively). Hence, upon cleavage at Arg$^{306}$ the A2 domain remains noncovalently associated with the A2 domain.

It has been shown that protein S is a cofactor for the inactivation of factor Va by APC only in the presence of a lipid bilayer, inducing a 2-fold increase in the rate of factor Va inactivation (24, 25). In addition, it has been demonstrated that factor Xa protects factor Va form APC inactivation in the presence of PCPS vesicles (16, 17). Thus, it has been concluded that only soluble factor Va molecules are inactivated by APC (25). These data demonstrate that only membrane-bound factor Va is efficiently inactivated by APC and that protein S does not alter the mechanism of the inactivation of the cofactor. These data partially explain the cofactor effect of protein S on APC inactivation (which is only expressed in the presence of a phospholipid surface) since the inactivating APC cleavage site at Arg$^{306}$ is only exposed on the membrane-bound cofactor. Thus, membrane-bound factor Va and not factor Va in solution is the substrate for inactivation by APC.

These data also show that the light chain of the cofactor is cleaved by APC in the absence and presence of PCPS vesicles at both Arg$^{1752}$ and Arg$^{1753}$ (FIG. 6 and Table 1). The resulting fragments differ by 1 amino acid at their NH$_2$ termini (i.e., RASSEVKNSH SEQUENCE I.D. NO.1 and ASSEVKNSH SEQUENCE I.D. NO.2). This nonpreferential cleavage of the light chain demonstrates a proteolytic "wobble" that has no consequence on factor Va cofactor activity and does not occur on either human factor Va or human factor VIIIa since the light chain of both human cofactors is not cleaved by APC in the presence of a lipid bilayer (50-52). The significance of the proteolytic wobble on the light chain is unclear and requires further investigation.

The importance of a phospholipid membrane acting as an "enhancing cofactor" for the propagation of the blood coagulation cascade has been demonstrated repeatedly for the conversion of prothrombin to thrombin via meizothrombin by factor Xa (56-59) and for the conversion of factor IX to factor IXα by factor Xa (60, 61). Both of these reactions require a phospholipid membrane for optimum efficiency. Bovine prothrombin is activated to α-thrombin by factor Xa after two cleavages ($Arg^{274}$ and $Arg^{323}$) in the absence as well as in the presence of a lipid bilayer. However, albeit the fact that in the absence of PCPS vesicles factor Xa alone can cleave prothrombin to generate α-thrombin, the rate of thrombin formation is 5 orders of magnitude slower than in the presence of phospholipid (2), and the mechanism of cleavaged proceeds through fragment 1.2 and prothrombin-2 (cleavage at $Arg^{274}$ followed by cleavage at $Arg^{323}$) (56). In contrast, factor Xa as a member of the prothrombinase complex associated on a membrane surface converts prothrombin to α-thrombin via the intermediated meizothrombin (the first cleavage at $Arg^{323}$ generates meizothrombin, whereas the second cleavage at $Arg^{274}$ produces fragment 1.2 and α-thrombin) (57,58). These conclusions were also strengthened by the observations that bovine Gla-deficient prothrombins that lack the totality or part of the lipid binding domain were converted to α-thrombin via prethrombin-2 (59). No meizothrombin intermediate was noticed in the latter studies using these abnormal molecules (59). Similarly, human factor Xa, in the presence of PCPS vesicles and $Ca^{2+}$, can cleave human factor IX to factor IXα. Factor IX activation occurs after two cleavages at $Arg^{145}$ and $Arg^{180}$ and proceeds through the intermediate factor IXα (60). In the absence of phospholipid vesicles no cleavage of factor IX by factor Xa was observed (60, 61).

The profound effect of a membrane surface has been also established on the inactivation of bovine factor Va by plasmin (62). Factor Va is only partially inactivated by plasmin in the absence of a membrane surface, whereas in the presence of PCPS vesicles, the cofactor is inactivated rapidly (62). Thus, acceleration of the inactivation of the cofactor by APC and/or plasmin and subsequent destruction of the clot are promoted locally by the formation of an adequate membrane surface generated as a result of vascular injury.

In summary, the data discussed herein demonstrate that membrane-bound factor Va is completely inactivated after three cleavages of the heavy chain of the cofactor at $Arg^{306}$, $Arg^{505}$, and $Arg^{662}$ (FIG. 9). In addition, these data show that the cleavage at $Arg^{306}$ is lipid-dependent and is the cleavage that is required for the complete inactivation of the cofactor. Finally, it has been discovered that cleavage at $Arg^{506}$ in the human sequence is yet another suitable marker for the diagnosis of thrombotic or hemorrhagic events.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLES

Materials and Reagents

Hepes, Q-Sepharose Fast Flow, Sepharose CL-4B, cyanogen bromide, bovine serum albumin, L-palmitoyl-2-oleoyl phosphatidylserine (PS), and L-palmitoyl-2-oleoyl phsophatidylcholine (PC) were purchased from Sigma. D-Phenylalanylprolylarginyl chloromethyl ketone was purchased from Calbiochem. The fluorescent thrombin inhibitor dansylarginine-N-(3-ethyl-1,5-pentanediyl)amide (DPA) and bovine APC were obtained as described previously (28,29) and were a gift of Dr. Paul Haley (Hematologic Technologies Inc., Essex Junction, Vt.). Bovine protein S was a gift of Dr. Walter Kisiel (Department of Pathology, University of New Mexico, School of Medicine, Albuquerque, N. Mex.). Bovine prothrombin, thrombin, and factor Xa were obtained according to methods described previously (30,31). Bovine factor Va and factor Va components were obtained as reported (32-34).

The $NH_2$-terminal amino acid sequences of the peptides were determined by automatic Edman degradation on an Applied Biosystems 475A protein sequencing system equipped with a Blott Cartridge in the laboratory of Dr. Alex Kurosky (University of Texas, Medical Branch at Galveston). The Phenylthiohydantoin derivatives were identified using HPLC and compared with a chromatogram containing all of the amino acids except cysteine.

Preparation of Phospholipid Vesicles

Phospholipid vesicles composed of 100% PC, 75% PC and 25% PS, and 100% PS were prepared as described previously (35). The concentration of the phospholipid vesicles within each mixture was determined by phosphorous assay (36).

Assay Measuring Thrombin Formation

The formation of thrombin was analyzed using the fluorescent thrombin inhibitor DAPA. The buffer used in all cases were composed of 20 Mm Hepes, 0.15M NaCl, 5 Mm $CaCl_2$, pH 7.4 ($HBS(Ca^{2+})$). In a typical experiment, a mixture containing prothrombin (1.4 μM), DAPA (3 μM), and phospholipid vesicles (20 μN) composed of 75% OC and 25% PS was incubated in the dark for 20 min. At selected time intervals an aliquot of the mixture (1,985 μl) was added to a cuvette containing 10 Nm factor Xa, and the base line was monitored for 15 s at room temperature using a Perkin-Elmer-Cetus Instruments MPF-44A fluorescence spectrophotometer with $\lambda_{ex}$ 280 nm, $\lambda_{em}$ 550 nm, and a 500-nm long pass filter in the emission beam.

Factor Va APC Cleavage Studies

Bovine factor Va (200 Nm) was incubated with APC (10 Nm) in the absence and presence of PCPS (15 μM) at 37° C. At selected time intervals aliquots of the mixture (10 μl) were added to the cuvette containing prothrombin, DAPA, PCPS, and the factor Xa, and the fluorescence intensity caused by the formation of thrombin and its complexation with DAPA was monitored with time (the final concentration of factor Va in the mixture was 1 Nm). Under these conditions the rate of thrombin formation is linearly related to the amount of active cofactor (factor Va). The initial rate of the formation of thrombin (Nm IIa·$min^{-1}$·$Nm^{-1}$) was calculated as described (28). At the same time intervals another aliquot of the mixture (140 μl) was mixed with 2% μ-mercaptoethanol, heated for 5 min at 90° C., and sorted at −20° C. prior to analysis by polyacrylamide gel electrophoresis (SDS-PAGE).

Cofactor Activity of Factor Xa-treated Factor Va

The factor Xa cleavage products of factor Va were prepared as follows. Bovine factor Va was incubated with bovine factor Xa (1:1 molar ratio, 48 h, 37° C.). Control experiments were performed using factor Va incubated at 37° C. for 48 h in the absence of factor Xa. The factor Va-factor Xa interaction is characterized by a $K_D$ of 0.8 μM in the absence of a lipid surface (22) and a $K_D$ of 1 Nm in the presence of PCPS vesicles (37). On the other hand the anti-factor X antibody, αBFX-2b, has a high affinity for bovine factor Xa in solution ($K_D$~$10^{-10}$M) (38). Thus, to immunopurify factor Xa from the factor Va-factor Xa mixture, factor Va was hydrolyzed by factor Xa in the absence of phospholipid vesicles. Consequently, in the absence of lipid and in the presence of factor Va and αBFX-2b, factor Xa will preferentially bind to the monoclonal antibody rather than to factor Va. The mixture was incubated with an excess of monoclonal antibody αBFX-2b coupled to Sepharose CL-4B (38). Following centrifugation (10,000 rpm, 5 min) the supernatant was analyzed by SDS-PAGE and assessed for cofactor activity in the presence and absence of APC as described above.

The cofactor effect of protein S on the APC inactivating activity was also tested. Protein S (20 and 40 nM) was incubated with APC (8 nM) ±PCPS vesicles (60 μM) for 10 min at room temperature (1 ml). The reaction was started by the addition of a solution of factor Va (800 nM, in 1 ml) to the APC mixture. The final concentrations of proteins were: 400 nM Factor Va, 4 nM APC, 30 μM PCPS vesicles, and 10 or 20 nM protein S. Experiments were also performed under the same conditions but in the absence of protein S. At selected time intervals aliquots of the mixture were withdrawn (5 μl) and assayed for cofactor activity as described above. Another aliquot (140 μl) was mixed with 2% SDS and 2% β-mercapthoethanol and heated for 5 min at 90° C. prior to analysis by SDS-PAGE. Control experiments were also performed in the absence of APC but in the presence of protein S, and in the absence of both, APC and protein S.

Gel Filtration an Ion Exchange Chromatography of APC-treated Membrane-bound Factor Va Membrane-bound factor Va (3 μM) was incubated with PCPS vesicles (200 μM) and APC (150 nM) in HBS($Ca^{2+}$) at 37° C. for 3 h. The mixture was then incubated with 50 mM EDTA for 16 h at room temperature. Following incubation with EDTA the mixture was applied to a QC-PAK GFC 7.8-mm×15-cm TSK high performance liquid chromatography (HPLC) gel filtration column (TosoHaas, Montgomery, Pa.) equilibrated in 20 mM Hepes, 0.15M NaCl (HBS), 10 mM EDTA, pH 7.4 Elution of fragment s was performed using the same buffer. The flow rate was 1 ml/min, and the column effluent was monitored at 280 nm with a Waters model 420 absorbance detector (Waters, Milford, Mass.). The data were collected on a strip chart recorder operated at 10 mm/min.

Ion exchange chromatography was performed using the fast protein liquid chromatography system (Pharmacia LKB Biotechnology Inc.) with a Mono Q HR 5/5 or a Mono S HR 5/5 column (Pharmacia). After APC digestion the membrane-bound cofactor was incubated with 50 nM EDTA and 0.1% Tween 20 (J. T. Baker) for 16 h at room temperature. The sample was injected to the column, and the column was washed with HBS, 10 mM EDTA. Fragments were eluted with a linear gradient of NaCl (0.15–1M) in 20 mM Hepes, 10 mM EDTA, pH 7.4. Fractions of 1.5 ml were collected and monitored for absorbance at 280/320 nm $CaCl_2$. The presence of the factor Va fragments in the various fractions was verified by SDS-PAGE.

Gel Electrophoresis-SDS-PAGE analysis was performed using 5–15% and 8–18% gradient gels according to the method of Laemmil (39). Densitometric analysis of the Coomassie Brilliant Blue-stained SDS-PAGE were performed using a Microscan 1000 scanning densitometer (TRI Inc., Nashville, Tenn.).

Electroblotting and Amino Acid Sequencing—An 8–18% gradient SDS-PAGE gel was used to analyze the proteolytic fragments resulting from the digestion of factor Va by APC in the absence or presence of PCPS vesicles. Usually the digestion was performed for 3 h at 37° C. using 50 μg of bovine factor Va at a 1:20 enzyme to substrate ratio (molar ratio). The samples were analyzed reduced and transferred to polyvinylidene difloride membrane using a modification of a method described previously (40). An Immobilon-P membrane (Millipore Corp.) was rinsed with 100% methanol and immersed in the transfer buffer (200 Mm glycine, 25 Mm Tris, 0.1% SDS, and 20% methanol). The gel was placed on the polyvinylidene difluoride membrane and covered with four sheets of chromatography paper (Whatman 3MM). A Trans-Blot SD semidry transfer cell (Bio-Rad) was used for the transfer, and the protein were electrocuted form the gel for 150 min at 250-mA constant current using a Safety Blotting Power Supply (Gelman Sciences, Ann Arbor, Mich.) Following transfer, the membrane was stained for 5 min with 0.25% Coomassie Blue R-250 in 50% methanol and 10% acetic acid (2×5 min), and finally the membrane was rinsed with distilled water (2×5 min), air dried overnight, and stored at −20° C.

CITED REFERENCES

The following references have been cited herein, and their contents are hereby incorporated by reference:

1. Mann et al., *Annu. Rev. Biochem.,* 57, 915–956, (1990).

2. Nesheim et al., *J. Biol. Chem.,* 254, 10952–10962, (1979).

3. Blomback et al., *Ann. N. Y. Acad. Sci.,* 202, 77–97 (1972).

4. Esmon et al., *J. Biol. Chem.,* 257, 859–864 (1982).

5. Kisiel et al., *Methods Enzymol.,* 80, 320–332 (1981).

6. Haley et al., *J. Biol. Chem.,* 264, 16303–16310.

7. Church et al., *Proc. Natl. Acad. Sci. U.S.A.,* 81, 6934–6937 (1984).

8. Kane et al., *Blood,* 71, 539–555 (1988).

9. Guinto et al., *J. Biol. Chem.,* 267, 2971–2978 (1992).

10. Nesheim et al., *J. Biol. Chem.,* 254, 1326–1334 (1979).

11. Foster et al., *J. Biol. Chem.,* 258, 13970–13977 (1983).

12. Monkovic et al., *Biochemistry,* 29, 1118–1128 (1990).

13. Esmon, C. T., *J. Biol. Chem.,* 254, 964–973, (1979).

14. Krishnaswamy et al., *J. Biol. Chem.,* 264, 3160–3168 (1989).

15. Kisiel et al., *Biochemistry,* 16, 5824–5831 (1977).

16. Walker et al., *Biochim. Biophys. Acta.,* 571, 333–342 (1979).

17. Nesheim et al.,*J. Biol Chem.,* 262, 1443–1447 (1982).

18. Guinto et al., *J. Biol. Chem.,* 259, 13986–13992 (1984).

19. Jane et al., *J. Clin. Invest.,* 83, 222–226 (1989).

20. Odegaard, et al., *J. Biol. Chem.,* 262, 11233–11238 (1987).

21. Kalafatis, et al., *Blood,* 81, 704–719 (1993).

22. Pyrzdial et al.,*J. Biol. Chem.,* 266, 8969–8977 (1991).

23. Luckow et al., *Biochemistry,* 28, 2348–2354 (1989).

24. Walker, F. J., *J. Biol. Chem.,* 255, 5521–5524 (1980).

25. Walker, F. J., *J. Biol. Chem.,* 256, 11128–11131 (1981).

26. Comp et al., *J. Clin. Invest.*, 74, 2082–2088 (1984).

27. Mannucci et al., *Thromb. Haemostasis*, 55, 440 (1986).

28. Nesheim et al., *Biochemistry*, 18, 996–1003 (1979).

29. Kisiel, W., *J. Clin. Invest.*, 64, 761–769 (1979).

30. Lundblad et al., *Methods Enzymol.*, 45, 156–0176 (1976).

31. Bajaj et al., *J. Biol. Chem.*, 248, 7729–7741 (1973).

32. Nesheim et al., *Methods Enzymol.*, 80, 243–275 (1980).

33. Katzmann et al., *Proc. Natl. Acad. Sci. U.S.A.*, 78, 162–166 (1981).

34. Kalafatis et al., *Methods Enzymol.*, 222, 224–236 (1993).

35. Barenholz et al., *Biochemistry*, 16, 2806–2910 (1977).

36. Gomori, G., *J. Lab. Clin. Med.*, 27, 955–960 (1942).

37. Krishnaswamy, S., *J. Biol. Chem.*, 265, 3708–3718 (1990).

38. Church et al., *Blood*, 72, 1911–1921 (1988).

39. Laemmli, U. K., *Nature*, 227, 680–685 (1970).

40. Matsudaira, P., *J. Biol. Chem.*, 262, 10035–10038 (1987).

41. Kalafatis et al., *Circulation*, 86, 1857 (abstr.) (1992).

42. Cutsforth et al., *Thromb. Haemostasis*, 65, 858 (abstr.) (1991).

43. Krishnaswamy et al., *J. Biol. Chem.*, 263, 5714–5723 (1988).

44. Higgins et al., *J. Biol. Chem.*, 258, 6503–6508 (1983).

45. Kalafatis et al., *J. Biol. Chem.*, 265, 21580–21589 (1990).

46. Ortel et al., *J. Biol. Chem.*, 267, 4189–4198 (1992).

47. Tracy et al., *J. Biol. Chem.*, 258, 662–669 (1983).

48. Krishnaswamy et al., *J. Biol. Chem.*, 261, 9684–9693 (1986).

49. Walker et al., *J. Biol. Chem.*, 265, 1484–1489 (1990).

50. Suzuki et al., *J. Biol. Chem.*, 258, 1914–1920 (1983).

51. Eaton et al., *Biochemistry*, 25, 505–512 (1986).

52. Fay et al., *J. Biol. Chem.*, 266, 20139–20145 (1991).

53. Pittman et al., *Proc. Natl. Acad. Sci. U.S.A.*, 85, 2429–2433 (1988).

54. Fay et al., *J. Biol. Chem.*, 266, 8957–8962 (1991).

55. Fay et al., *J. Biol. Chem.*, 267, 13246–13250 (1992).

56. Heldebrandt al., *J. Biol. Chem.*, 248, 7149–7163 (1992).

57. Nesheim et al., *J. Biol. Chem.*, 258, 5386–5391 (1983).

58. Krishnaswamy et al., *J. Biol. Chem.*, 261, 8977–8984 (1986).

59. Malhotra et al., *J. Biol. Chem.*, 260, 279–287 (1985).

60. Lawson et al., *J. Biol. Chem.*, 266, 11317–11327 (1991).

61. Kalousek et al., *FEBS Lett.*, 50, 382–385 (1975).

62. Omar et al., *J. Biol. Chem.*, 262, 9750–9755 (1987).

63. Xue et al., *Biochemistry*, 32, 5917–5923 (1993).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

---

What is claimed is:

1. A method of detecting factor Va related thrombotic or hemorrhagic events in a mammal, the method comprising:
   a) obtaining blood or plasma from the mammal; and
   b) monitoring by an immunoassay the mammalian blood or plasma for one or more fragments of factor Va selected from the group consisting of the cleavage fragments of the heavy chain at $Arg^{306}$ and $Arg^{506}$ wherein the cleavage fragments include fragments having residues 1–306 and 307–506 of factor Va,
   wherein the detection of the one or more fragments is indicative of the thrombotic or hemorrhagic events in the mammal.

2. A method of detecting factor Va related thrombotic or hemorrhagic events in a mammal, the method comprising:
   a) obtaining blood or plasma from the mammal; and
   b) monitoring by an immunoassay the mammalian blood or plasma for one or more fragments of factor Va selected from cleavage fragments of the heavy chain at $Arg^{306}$,
   wherein the detection of the one or more fragments is indicative of the thrombotic or hemorrhagic events in the mammal.

3. The method of claim 2, wherein one of the cleavage fragments has an N-terminus at residue 307.

* * * * *